United States Patent [19]

Srivastava

[11] Patent Number: 5,961,979
[45] Date of Patent: Oct. 5, 1999

[54] STRESS PROTEIN-PEPTIDE COMPLEXES AS PROPHYLACTIC AND THERAPEUTIC VACCINES AGAINST INTRACELLULAR PATHOGENS

[75] Inventor: Pramod K. Srivastava, Riverdale, N.Y.

[73] Assignee: Mount Sinai School of Medicine of the City University of New York, New York, N.Y.

[21] Appl. No.: 08/210,421

[22] Filed: Mar. 16, 1994

[51] Int. Cl.$^6$ .......................... A61K 39/02; A61K 39/12; A61K 39/385

[52] U.S. Cl. ..................................... 424/193.1; 424/190.1; 424/191.1; 424/192.1; 424/196.11; 424/197.11; 514/2; 514/21; 530/412

[58] Field of Search ....................... 514/2, 21; 424/193.1, 424/185.1, 190.1, 191.1, 192.1, 196.11, 197.11; 530/412

[56] References Cited

U.S. PATENT DOCUMENTS

| | | |
|---|---|---|
| 5,188,964 | 2/1993 | McGuire et al. . |
| 5,232,833 | 8/1993 | Sanders et al. . |
| 5,288,639 | 2/1994 | Burnie et al. ........................ 435/320.1 |

FOREIGN PATENT DOCUMENTS

| | | |
|---|---|---|
| 196 02 985 A1 | 7/1997 | Germany . |
| 2 251 186 | 7/1992 | United Kingdom . |
| WO 89/12455 | 12/1989 | WIPO . |
| WO 90/02564 | 3/1990 | WIPO . |
| WO 91/15572 | 10/1991 | WIPO . |
| WO 92/01717 | 2/1992 | WIPO . |
| WO 92/08484 | 5/1992 | WIPO . |
| WO 92/08488 | 5/1992 | WIPO . |
| WO 93/14118 | 7/1993 | WIPO . |
| WO 93/17712 | 9/1993 | WIPO . |
| WO 93/18146 | 9/1993 | WIPO . |
| WO 93/18147 | 9/1993 | WIPO . |
| WO 93/18150 | 9/1993 | WIPO . |
| WO 93/21529 | 10/1993 | WIPO . |
| WO 93/24136 | 12/1993 | WIPO . |
| WO 94/03208 | 2/1994 | WIPO . |
| WO 94/03599 | 2/1994 | WIPO . |
| WO 94/04676 | 3/1994 | WIPO . |
| 97/06685 | 2/1997 | WIPO . |
| WO 97/06821 | 2/1997 | WIPO . |
| WO 97/06828 | 2/1997 | WIPO . |
| WO 97/26910 | 7/1997 | WIPO . |

OTHER PUBLICATIONS

Abe et al., "Different susceptibility to the IL-3 induced-protective effects between *Strongyloides ratti* and *Nippostrongylus brasiliensis* in C57BL/6 mice", Parasite Immunol. (1993) 15:643–645.

Durum and Oppenheim, "Proinflammatory cytokines and immunity", in Chapter 21 of *Fundamental Immunology*, 3d Ed., edited by William E. Paul, Raven Press, LTD., New York (1993) pp. 820–822.

Finkelman et al., "Regulation and biological function of helminth–induced cytokine responses", Immunol. Today (1991) 12:A62–A66.

Grenics et al., "Host protective immunity to *Trichinella spiralis* in mice: activation of Th cell subsets and lymphokine secretion in mice expressing different response phenotypes", Immunol. (1991) 74:329–332.

Howard et al., "T–cell–derived cytokines and their receptors", in Chapter 20 of *Fundamental Immunology*, 3d Ed., edited by William E. Paul, Raven Press, Ltd., New York (1993) pp. 763–776.

Korenaga et al., "The role of interleukin–5 in protective immunity to *Strongyloides venezuelensis* infection in mice", Immunol. (1991) 72:502–507.

Lotz and Seth, "TGFβ and HIV infection", Ann. N.Y. Acad. Sci. (1993) 685:501–511.

Murray, "Gamma interferon, cytokine–induced macrophage activation, and antimicrobial host defense", Diagn. Microbiol. Infect. Dis. (1990) 13:411–421.

Murray, "Cytokines as antimicrobial therapy for the T cell deficient patient: prospects for treatment of nonviral opportunistic infections", Clin. Infect. Dis. (1993) 17:S407–413.

Swain et al., "Transforming growth factor–beta and IL–4 cause helper T cell precursors to develop into distinct effector helper cells that differ in lymphokine secretion pattern and cell surface pphenotype", J. Immunol. (1991) 1:2991–3000.

Troye–Blomberg et al., "T–cell control of immunity to the asexual blood stages of the malaria parasite", Crit. Rev. Immunol. (1994) 14:131–155.

Urban, Jr. et al., "The importance of Th2 cytokines in protective immunity to nematodes", Immunol. Rev. (1992) 127:205–220.

Yin et al., "Enhancement of in vitro and in vivo antigen–specific antibody responses by interleukin 11", J. Exp. Med. (1992) 175:211–216.

Afonso et al., "The Adjuvant Effect of Interleukin–12 in a Vaccine Against *Leishmania major*", Science (1994) 263:235–237.

S.K. Durum and J.J. Oppenheim, "Proinflammatory Cytokines and Immunity", in Chapter 21 of *Fundamental Immunology*, 3d Ed., edited by William E. Paul, Raven Pres, Ltd., New York, (1993) pp. 801 and 815–819.

Hakim et at., "CD8+ T cells from mice vaccinated against *Toxoplasma gondii* are cytotoxic for parasite–infected or antigen–pulsed host cells" J. Immunol. (1991), 147:2310–2316.

Kaufmann, "Immunity to Intracellular Bacteria", Annu. Rev. Immunol. (1993) 11:129–163.

(List continued on next page.)

*Primary Examiner*—Paula K. Hutzell
*Assistant Examiner*—Geetha P. Bansal
*Attorney, Agent, or Firm*—Pennie & Edmonds LLP

[57] ABSTRACT

Disclosed is a family of vaccines that contain stress protein-peptide complexes which when administered to a mammal are operative at initiating in the mammal cytotoxic T cell responses against preselected intracellular pathogens. Also disclosed are methodologies for preparing and administering vaccines containing stress protein-peptide complexes.

153 Claims, 3 Drawing Sheets

OTHER PUBLICATIONS

Kaufmann, "CD8+ T lymphocytes in intracellular microbial infections", Immunology Today (1988) 9:168–174.

Nieland et al., Isolation of an immunodominant viral peptide that is endogenously bound to the stress protein GP96/GR94, Proc. Natl. Acad. Sci. USA, (1996) 93:6135–6139.

P.A. Scott and A. Sher, "Immunoparasitology" in Chapter 33, of Fundamental Immunology, Third Edition, 1993, edited by William E. Paul, Raven Press, Ltd., New York, pp. 1179, and 1188–1189.

Blachere et al. J. Immunother. 14:352–356, 1993.

Subbarao & Murphy, Genetically Engineered Vaccines, Ciardi et al. (eds.) Plenum Press, NY, pp. 51–57, 1992.

Young, R.A. Ann. Rev. Immunol. 8:401–430, 1990.

Li & Srivastava, EMBO J. 12:3143–51, 1993.

Udono & Srivastava, J. Immunol. 152:5398–5403, 1994.

Srivastava & Heike, Sem. Immunol. 3(1):57064, 1991.

Browning et al. Cell 72:847–56, 1993.

Welch, W.J. (May, 1993) "How Cells Respond to Stress", *Scientific American* pp. 56–64.

Franklin, C. (1993) "Making vaccines fit the cancer" *New Scientist*, vol. 140, p. 17.

Udono et al. (1993) "Heat Shock Protein 70–assocaited Peptides Elicit Specific Cancer Immunity", *J. Exp. Med.* 178:1391–1396.

Blachere et al. (1993) "Immunization with GP96 Heat Shock Proteins Isolated from Tumors or Influenza Virus Infected Cells Elicits MHC—Restricted, Antigen—Specific Cytotoxic T Lymphocyes Against the Corresponding Cells/Antigens" Abstract presented at the UCLA Symposium, Taos, New Mexico, Mar. 17–24, 1993, Cellular Immunity and the Immunotherapy of Cancer, *J. Cellular Biochem.* 17D:124.

Salk et al. (1993) "A Strategy for Prophylactic Vaccination Against HIV", *Science* 260:1270–1272.

Aldovini et al. (1992) "The New Vaccines", *Technology Review* pp. 24–31.

Lussow et al. (1991) "Mycobacterial Heat–shock Proteins as Carrier Molecules", *Eur. J. Immunol.* 21:2297–2302.

Barrios et al. (1992) "Mycobacterial Heat–shock Proteins as Carrier Molecules. II: The Use of the 70–kDa Mycobacterial Heat–shock Proteins as Carrier for Conjugated Vaccines can Circumvent the need for Adjuvants and Bacillus Calmette Guérin Priming", *Eur. J. Immunol.* 22:1365–1372.

Rothman, J.E. (1989) "Polypeptide Chain Binding Proteins: Catalysts of Protein Folding and Related Processes in Cells", *Cell* 59:591–601.

Flynn et al. (1991) "Peptide–binding Specificity of the Molecular Chaperone BiP", *Nature* 353:726–730.

Craig, E.A. (1993) "Chaperones: Helpers Along the Pathways to Protein Folding", *Science* 260:1902–1904.

Gething et al. (1992) "Protein Folding in the Cell", *Nature* 355:33–45.

Lindquist et al. (1988) "The Heat–Shock Proteins", *Annu. Rev. Genet.* 22:631–677.

Welch et al. (1985) "Rapid Purification of Mammalian 70,000–Dalton Stress Proteins: Affinity of the Proteins for Nucleotides", *Mol. Cell. Biol.* 5:1229–1237.

Jakob et al. (1993) "Small Heat Shock Proteins Are Molecular Chaperones", *The Journal of Biological Chemistry* 268:1517–1520.

Lukacs et al. (1993) "Tumor Cells Transfected with a Bacterial Heat–Shock Gene Lose Tumorigenicity and Induce Protection against Tumors", *J. Exp. Med.* 178: 343–348.

Viitanen et al. (1992) "Mammalian Mitochondrial Chaperonin 60 Functions as a Single Toroidal Ring", *The Journal of Biological Chemistry* 267: 695–698.

Lévy, F. (1991) "ATP is Required for in Vitro Assembly of MHC Class I Antigens but Not for Transfer of Peptides across the ER Membrane", *Cell* 67:265–274.

Srivastava et al. (1986) "Tumor Rejection Antigens of Chemically Induced Sarcomas of Inbred Mice", *Proc. Natl. Acad. Sci. USA* 83:3407–3411.

Madden et al. (1991) "The Structure of HLA–B27 Reveals Nonamer Self–peptides Bound in an Extended Conformation" *Nature* 353:321–325.

Yu Rudensky et al. (1991) "Sequence Analysis of Peptides Bound to MHC Class II Molecules", *Nature* 353:622–627.

Nelson et al. (1992) "The Translation Machinery and 70 kd Heat Shock Protein Cooperate in Protein Synthesis", *Cell* 71:97–105.

McCall et al. (1989) "Biotherapy: A New Dimension in Cancer Treatment", *Biotechnology* 7:231–240.

Luescher et al. (1991) "Specific Binding of Antigenic Peptides to Cell– associated MHC Class I Molecules", *Nature* 351:72–77.

Schumacher et al. (1991) "Peptide Selection by MHC Class I Molecules", *Nature* 350:703–706.

Falk et al. (1991) "Allele–specific Motifs Revealed by Sequencing of Self–peptides Eluted from MHC Molecules", *Nature* 351:290–296.

Rötzschke et al. (1990) "Isolation and Analysis of Naturally Processed Viral Peptides as Recognized by Cytotoxic T. cells", *Nature* 348:252–254.

Falk et al. (1990) "Cellular Peptide Composition Governed by Major Histocompatibliity Complex Class I Molecules", *Nature* 348:248–251.

Jardetzky et al., (1991) "Identification of Self Peptides Bound to Purified HLA–B27", *Nature* 353:326–329.

Elliott et al. (1990) "Naturally Processed Peptides", *Nature* 348:195–197.

Subbarao et al. (1992) "A General Overview of Viral Vaccine Development", *Genetically Engineered Vaccines* 327:51–57.

Melnick J.L. (1985) "Virus Vaccines: An Overview", Proceedings of the First Annual Southwest Foundation for Biomedical Research International Symposium, Houston, Texas, Nov. 8–10, 1984 *American Society for Microbiology* pp. 1–13.

Vogue (Mar. 1994) Health News p. 258.

Srivastava, P.K. (1991) "Protein Tumor Antigens" Current Opinion in Immunology, *Cancer* 3:654–658.

Srivastava, et al. (1984) "The Serologically Unique Cell Surface Antigen of Zajdela Ascitic Hepatoma is also its Tumor–Associated Transplantation Antigen", *Int. J. Cancer* 33:417–422.

Srivastava et al. (1993) "Peptide–Binding Heat Shock Proteins in the Endoplasmic Reticulum: Role in Immune Response to Cancer and in Antigen Presentation", *Advances in Cancer Research* 62:153–177.

Srivastava et al. (1991) "Stress–Induced Proteins in Immune Response to Cancer", *Current Topics in Microbiology and Immunology* 167:109–123.

Srivastava et al. (1994) "Heat Shock Proteins Transfer Peptides During Antigen Processing and CTL Priming", *Immunogenetics* 39:93–98.

Palladino, Jr., et al. (1987) "Expression of a Shared Tumor–specific Antigen by Two Chemically Induced BALB/c Sarcomas[1]", *Cancer Research* 47:5074–5079.

Srivastava et al. (1988) "Individually Distinct Transplantation Antigens of Chemically Induced Mouse", *Immunology Today* 9:78–83.

Welch et al. (1982) "Purification of the Major Mammalian Heat Shock Proteins", *J Biol Chem* 257:14949–14959.

Srivastava et al. (Mar. 13, 1993) "Evidence for peptide–chaperoning by the endoplasmic reticular heat shock protein GP96: Implications for vaccination against cancer and infectious diseases", J Cell Biochem Suppl 17D:94 (Abstract NZ014).

Thomas et al. (1982) "Molecular and Cellular Effects of Heat Shock and Related Treatments of Mammalian Tissue–Culture Cells", Cold Springs Harbor Symp Quant Biol 46:985–996.

Levinson et al. (1979) "Metal Binding Drugs Induce Synthesis of Four Proteins in Normal Cells", Biol Trace Element Research 1:15–23.

Basombrio (1970) "Search for common antigenicities among twenty–five sarcomas induced by methylcholanthrene", *The Institute for Cancer Resarch* 30:2458–2462.

Bensaude et al. (1983) "Spontaneous high expression of heat–shock proteins in mouse embryonal carcinoma cells and ectoderm for day 8 mouse embryo", *EMBO J.* 2:173–177.

Boon (1992) "Toward a genetic analysis of tumor rejection antigens", *Advances Cancer Res.* 58:177–210.

Cohen (1993) "Cancer vaccines get a shot in the arm", *Science* 262:841–843.

Ebert et al. (1987) "Characterization of an immunosuppressive factor derived from colon cancer cells", *J. Immunol.* 138(7):2161–2168.

Feldweg et al. (1993) "Evidence for biochemical heterogeneity of gp96 heat shock protein/tumor rejection antigen", *J. Cell. Biochem. Suppl.* 17D:108 (abs).

Flynn et al. (1989) "Peptide binding and release by proteins implicated as catalysts of protein assembly", *Science* 245:385–390.

Globerson and Feldman (1964) "Antigenic Specificity of Benzo[a]pyrene–Induced Sacomas", *Journal of National Cancer Institute* 32(6):1229–1242.

Huber et al. (1992) "Protease inhibitors ingerfere with the transforming factor–β–dependent but not transforming growth factor–β–independent pathway of tumor cell–mediated immunosuppression", *J. Immunol.* 148(1):277–284.

Lakey et al. (1987) "Identification of a peptide binding protein that plays a role in antigen presentation", *Proc. Natl. Acad. Sci. USA* 84:1659–1663.

Lanzavecchi (1993) "Identifying Strategies for Immune Intervention", *Science* 260:937–944.

Maki et al. (1990) "Human homologue of murine tumor rejection antigen gp96: 5'–Regulatory and coding regions and relationship to stress–induced proteins", *Proc. Natl. Acad. Sci. USA* 87:5658–5663.

Maki et al. (1993) Mapping of the Genes for Human Endoplasmic Reticular Heat Shock Protein gp96/grp94, *Somatic Cell Mol. Genetic* 19(1):73–81.

Mizoguchi et al. (1992) "Alterations in signal transduction molecules in T lymphocytes from tumor–bearing mice", *Science* 258:1795–1798.

Prehn et al. (1957) "Immunity to Methylcholanthrene–induced sarcomas", *J. Cancer Institute* 18:769–778.

Srivastava et al. (1987) "5'–Structural analysis of genes encoding polymorphic antigens of chemically induced tumors", *Proc. Natl. Acad. Sci. USA* 84:3807–3811.

Srivastava et al. (1988) "Chromosonal Assignment of the Gene Encoding the Mouse Tumor Rejection Antigen gp96", *Immunogenetics* 28:205–207.

Srivastava et al. (1989) "Identification of a Human Homologue of the Murine Tumor Rejection Antigen GP96", *Cancer Research* 49:1341–1343.

Szikora et al. (1990) "Structure of the gene of tum–transplanation antigen P35B presence of a point mutation in the antigenic allele", *The EMBO Journal* 9(4):1041–1050.

Udono (1993) "Heat shock proteins HSP70, HSP90 and GP96 elicit tumor specific immunity to the tumors from which they are isolated", *J. Cell. Biochem.* Suppl. 17D:113 (Abstract NZ225).

Ullrich et al. (1986) "A mount tumor–specific transplantation antigen is a heat shock–related protein", *Proc. Natl. Acad. Sci.* 83:3121–3125.

Van den Enyde et al. (1991) "The gene coding for a major tumor rejection antigen of tumor P815 is identical to the normal gene of syngeneic DBA/2 mice", *J. Exp. Med.* 173:1373–1384.

Vanbuskirk et al. (1989) "A peptide binding protein having a role in antigen presentation is a member of the hsp70 heat shock family", *J. Exp. Med.* 170:1799–1809.

STRESS PROTEIN-PEPTIDE COMPLEXES AS PROPHYLACTIC AND THERAPEUTIC VACCINES AGAINST INTRACELLULAR PATHOGENS

This invention was made with government support under grant number CA44786 awarded by the National Institutes of Health. The government has certain rights in the invention.

FIELD OF THE INVENTION

The application relates generally to the field of vaccine development, in particular, prophylactic and therapeutic vaccines effective against intracellular pathogens.

BACKGROUND OF THE INVENTION

Improved methodologies for developing vaccines directed against intracellular pathogens, for example, viruses, bacteria, protozoa, fungi, and intracellular parasites, is an ongoing effort in the art. The development and use of vaccines has proved invaluable in preventing the spread of disease in man. For example, in 1967, smallpox was endemic in 33 countries with 10 to 15 million cases being reported annually. At that time, the World Health Organization introduced a program to eradicate smallpox. Approximately one decade later smallpox was successfully eradicated from the human population.

In principle, a perfect vaccine would have a long shelf life and would be: capable of inducing in a mammal, with a single dose, long lasting immunity against a preselected pathogen and all of its phenotypic variants; incapable of causing the disease to which the vaccine was directed against; effective prophylactically and therapeutically; prepared easily and economically using standard methodologies; and administered in the field easily.

Presently there are four major classes of vaccine which have been developed against mammalian diseases. These include: live-attenuated vaccines; non-living whole vaccines; vector vaccines; and subunit vaccines. Several reviews discuss the preparation and utility of these classes of vaccines. See for example, Subbarao et al. (1992) in *Genetically Engineered Vaccines*, edited by Ciardi et al., Plenum Press, New York; and Melnick (1985) in *High Technology Route to Virus Vaccines*, edited by Dreesman et al., published by the American Society for Microbiology, the disclosures of which are incorporated herein by reference. A summary of the advantages and disadvantages of each of the four classes of vaccines is set forth below.

Live attenuated vaccines comprise live but attenuated, i.e., non-virulent, pathogens that have been "crippled" by means of genetic mutations. The mutations prevent the pathogens from causing disease in the recipient or vaccinee. The primary advantage of this type of vaccine is that the attenuated organism stimulates the immune system of the recipient in the same manner as the wild type pathogen by mimicking the natural infection. Furthermore, the attenuated pathogens replicate in the vaccinee thereby presenting a continuous supply of antigenic determinants to the recipient's immune system. As a result live vaccines can induce strong, long lasting immune responses against the wild type pathogen. In addition, live vaccines can stimulate the production of antibodies which neutralize the pathogen. Also they can induce resistance to the pathogen at its natural portal of entry into the host. To date, live attenuated vaccines have been developed against: smallpox; yellow fever; measles; mumps; rubella; poliomyelitis; adenovirus; and tuberculosis.

However, live attenuated vaccines have several inherent problems. First, there is always a risk that the attenuated pathogen may revert back to a virulent phenotype. In the event of phenotypic reversion, the vaccine may actually induce the disease it was designed to provide immunity against. Secondly, it is expensive and can be impractical to develop live vaccines directed against pathogens that continuously change their antigenic determinants. For example, researchers have been unable to develop a practical live vaccine against the influenza virus since the virus continually changes the antigenic determinants of its coat proteins. Thirdly, live attenuated vaccines cannot be developed against infections caused by retroviruses and transforming viruses. The nucleic acids from these viruses may integrate into the recipients genome with the potential risk of inducing cancer in the recipient. Fourthly, during the manufacture of live attenuated vaccines unrecognized adventitious agents present in the cells in which the vaccine is manufactured may be copurified along with the attenuated pathogen. Alien viruses that have already been detected in vaccine preparations have included the avian leukosis virus, the simian papovavirus SV40, and the simian cytomegalovirus. Fifthly, live vaccine preparations can be unstable therefore limiting their storage and use in the field. Attempts are presently being made to develop stabilizing agents which enhance the longevity of the active vaccines.

Non-living whole vaccines comprise non viable whole organisms. The pathogens are routinely inactivated either by chemical treatment, i.e., formalin inactivation, or by treatment with lethal doses of radiation. Non-living whole vaccines have been successfully developed against: pertussis; typhus; typhoid fever; paratyphoid fever; and particular strains of influenza.

In principle, non-living vaccines are usually safe to administer since it is unlikely that the organisms will cause disease in the individual. Furthermore, since the organism is dead the vaccines tend to be stable and have long shelf lives. There are, however, several disadvantages associated with non-living whole vaccines. First, extreme care is required in their manufacture to ensure that no live pathogens remain in the vaccine. Secondly, vaccines of this type are generally ineffective at stimulating cellular responses and tend to be ineffective against intracellular pathogens. Thirdly, the immunity elicited by non-viable vaccines is usually short lived and must be boosted at a later date. This process entails repeatedly reaching the persons in need of vaccination and also raises the concern about hypersensitizing the vaccinee against the wild type pathogen.

Vector vaccines, also known as live recombinant vehicle vaccines, are prepared by incorporating a gene encoding a specific antigenic determinant of interest into a living but harmless virus or bacterium. The harmless vector organism is in turn be injected into the intended recipient. In principle, the recombinant vector organism replicates in the host producing and presenting the antigenic determinant to the host's immune system. It is contemplated that this type of vaccine will be more effective than the non-replicative type of vaccine. For such a vaccine to be successful, the vector must be viable, and either be naturally non-virulent or have an attenuated phenotype.

Currently preferred vectors include specific strains of: vaccinia (cowpox) virus, adenovirus, adeno-associated virus, salmonella and mycobacteria. Live strains of vaccinia virus and mycobacteria have been administered safely to humans in the forms of the smallpox and tuberculosis (BCG) vaccines, respectively. They have been shown to express foreign proteins and exhibit little or no conversion into virulent phenotypes. Several types of vector vaccines using the BCG vector are currently being developed against the human immunodeficiency virus (HIV). For example, the HIV antigenic proteins: gag; env; HIV protease; reverse transcriptase; gp120 and gp41 have been introduced, one at a time, into the BCG vector and shown to induce T-cell mediated immune responses against the HIV proteins in animal models [Aldovini et al. (1991) *Nature* 351:479–482; Stover et al. (1991) *Nature* 351:456–460; Colston (1991) *Nature* 351:442–443].

Vector vaccines are capable of carrying a plurality of foreign genes thereby permitting simultaneous vaccination against a variety of preselected antigenic determinants. For example, researchers have engineered several HIV genes into the vaccinia virus genome thereby creating multivalent vaccines which are, in theory, capable of simultaneously stimulating a response against several HIV proteins.

There are several disadvantages associated with vector vaccines. First, it is necessary to identify suitable strains of viable but non pathogenic organisms that may act as carriers for the genes of interest. Secondly, vector vaccines can be prepared only when potentially protective antigenic determinants have been identified and characterized. Consequently, vector vaccines cannot be prepared against pathogens whose antigenic determinants have not yet been identified or are so variable that the prospect of identifying the antigenic determinant for each variant is impractical. Thirdly, the genes encoding the preselected antigenic determinant must be stably transfected and expressed in the preferred carrier organism. Consequently, the methodologies required for developing this type of vaccine are both labor intensive and time consuming. Fourthly, it has not yet been established that recombinant vector vaccines effectively immunize a recipient against a preselected pathogen.

Subunit vaccines usually comprise a subcellular component purified from the pathogen of interest. Subunit vaccines are usually safe to administer since it is unlikely that the subcellular components will cause disease in the recipient. The purified subcellular component may be either a defined subcellular fraction, purified protein, nucleic acid or polysaccharide having an antigenic determinant capable of stimulating an immune response against the pathogen. The antigenic components can be purified from a preparation of disrupted pathogens. Alternatively, the antigenic proteins, nucleic acids or polysaccharides may be synthesized using procedures well known in the art. Diseases that have been treated with subunit type vaccines include: cholera; diphtheria; hepatitis type B; poliomyelitis; tetanus; and specific strains of influenza.

There are several disadvantages associated with subunit vaccines. First, it is important to identify and characterize the protective antigenic determinant. This can be a labor intensive and time consuming process. As a result it may be impractical to develop subunit vaccines against pathogens with highly variable antigenic determinants. Secondly, subunit vaccines are generally ineffective at stimulating cytotoxic T cell responses and so they tend to be ineffective against intracellular pathogens. Thirdly, the immunity elicited by subunit vaccines is usually short lived and like the non-living whole vaccines must be boosted at a later date therefore raising the concern about hypersensitizing the vaccinee against the wild type pathogen.

To date, many of the inactivated whole and subunit vaccines have not been sufficiently immunogenic by themselves to induce strong, protective responses. As a result, immunostimulants including: aluminum hydroxide; intact mycobacteria; and mycobacterial components, have been coadministered with these vaccines to enhance the immune response stimulated by the vaccine. Recently, it has been shown that mycobacterial heat shock proteins may act as carriers for peptide vaccines enhancing the immunogenicity of the peptides in vivo [Lussow et al. (1991) *Eur. J. Immunol.* 21:2297–2302]. Further studies revealed that administering to mice a composition comprising an antigenic peptide chemically crosslinked to a purified mycobacterial stress protein stimulates a humoral (antibody mediated) rather than a temporal (cell mediated) response against the antigenic peptide [Barrios et al. (1992) *Eur. J. Immunol.* 22:1365–1372].

However, since it is generally believed that cellular responses are required for immunizing against intracellular pathogens (See for example, "Advanced Immunology," Male et al. (1991) Gower Medical Publishing) it is contemplated that conventional subunit and inactivated whole organism vaccines may be ineffective at stimulating immune responses, specifically cytotoxic T cell responses, against intracellular pathogens.

It is an object of the instant invention to provide a safe subunit vaccine comprising a stress protein-peptide complex for administration to a mammal that is capable of inducing, by means of a cytotoxic T cell response, resistance to infection by a preselected intracellular pathogen. The vaccines prepared in accordance with the invention are ideal for eliciting immune responses against diseases caused by intracellular pathogens whose protective antigenic determinants have not yet been identified, or where it is impractical to identify all the antigenic determinants of highly variable pathogens. The vaccines prepared in accordance with the invention may be prophylactically and therapeutically effective against preselected pathogens.

It is another object of the invention to provide a method for inducing in a mammal resistance to infection by an intracellular pathogen by administering to the mammal a stress protein-peptide subunit vaccine. Yet another object is to provide a method for rapidly and cost effectively producing commercially feasible quantities of the stress protein-peptide vaccines from either a cell or cell line infected with the intracellular pathogen. Still another object is to provide a method for preparing an immunogenic stress protein-peptide subunit vaccine by reconstituting in vitro immunologically unreactive stress proteins and peptides thereby to generate immunoreactive complexes capable of stimulating an immune response against a preselected intracellular pathogen.

These and other objects and features of the invention will be apparent from the description, drawings, and claims which follow.

SUMMARY OF THE INVENTION

It has now been discovered that a subunit vaccine containing a stress protein-peptide complex isolated from cells infected with a preselected intracellular pathogen when administered to a mammal can effectively stimulate cellular immune responses against cells infected with the same pathogen. Specifically, the immune response is mediated primarily through the cytotoxic T cell cascade which targets and destroys cells containing intracellular pathogens.

The vaccines prepared in accordance with the methodologies described herein provide an alternative approach for stimulating cellular immunity obviating the use of live (attenuated or otherwise) intracellular pathogens. In addition, the vaccines described herein are ideal for inducing immune responses against intracellular pathogens having undefined immunogenic determinants and for intracellular pathogens having a variety of phenotype variants making the identification of all antigenic determinants impractical.

A preferred embodiment of the invention comprises a vaccine that can be administered to a mammal for inducing in the mammal a cytotoxic T cell response against a preselected intracellular pathogen. Also it is also contemplated that the vaccines will induce in the mammal, by means of a cytotoxic T cell response, resistance to infection by the preselected intracellular pathogen. The vaccines manufactured in accordance with the principles described herein contain an immunogenic stress protein-peptide complex that is capable of stimulating in the recipient a cytotoxic T cell response directed against cells infected with the pathogen of interest. The complex may be administered to a mammal when combined with a pharmaceutically acceptable carrier, adjuvant, or excipient using techniques well known in the art. It is contemplated that the vaccines will have particular utility in stimulating immunity against a variety of mammalian diseases caused by intracellular pathogens such as viruses, bacteria, fungi, protozoa, and intracellular parasites.

The term "vaccine", as used herein, is understood to mean any composition containing a stress protein-peptide complex having at least one antigenic determinant which when administered to a mammal stimulates in the mammal an immune response against the antigenic determinant.

The term "stress protein" as used herein, is understood to mean any cellular protein which satisfies the following criteria. It is a protein whose intracellular concentration increases when a cell is exposed to stressful stimuli, it is capable of binding other proteins or peptides, and it is capable of releasing the bound proteins or peptides in the presence of adenosine triphosphate (ATP) or low pH. Stressful stimuli include, but are not limited to, heat shock, nutrient deprivation, metabolic disruption, oxygen radicals, and infection with intracellular pathogens.

It will be apparent to the artisan upon reading this disclosure that other recombinant stress proteins, including non native forms, truncated analogs, muteins, fusion proteins as well as other proteins capable of mimicking the peptide binding and immunogenic properties of a stress protein may be used in the preparation of stress protein-peptide vaccines disclosed herein.

The first stress proteins to be identified were the heat shock proteins (Hsp). As their name suggests, Hsps' are induced by a cell in response to heat shock. Three major families of Hsp have been identified, according to molecular weight, and have been called Hsp60, Hsp70 and Hsp90. The numbers reflect the approximate molecular weight of the stress proteins in kilodaltons. Many members of these families were found subsequently to be induced in response to other stressful stimuli, like those mentioned above.

Stress proteins are found in all prokaryotes and eukaryotes and exhibit a remarkable level of evolutionary conservation. For example, DnaK, the Hsp70 from *E. coli* has about 50% amino acid sequence identity with Hsp70 proteins from eukaryotes [Bardwell et al. (1984) *Proc. Natl. Acad. Sci.* 81:848–852]. The Hsp60 and Hsp90 families also exhibit similarly high levels of intrafamilial conservation [Hickey et al. (1989) *Mol. Cell Biol.* 9:2615–2626; Jindal (1989) *Mol. Cell. Biol.* 9:2279–2283]. In addition, it has been discovered that the Hsp-60, Hsp-70 and Hsp-90 families are composed of proteins that are related to the stress proteins in sequence, for example, having greater than 35% amino acid identity, but whose expression levels are not altered by stress. Accordingly, it is contemplated that the definition of stress protein, as used herein, embraces other proteins, muteins, analogs, and variants thereof having at least 35% to 55%, preferably 55% to 75%, and most preferably 75% to 85% amino acid identity with members of the three families whose expression levels in a cell are stimulated in response to stressful stimuli.

The term "peptide", as used herein, is understood to mean any amino acid sequence present in a eukaryotic cell infected with an intracellular pathogen but not present when the cell is not infected with the same pathogen. The definition embraces peptides that not only originate from the pathogen itself but also peptides which are synthesized by the infected cell in response to infection by the intracellular pathogen.

The term "immunogenic stress protein-peptide complex", as used herein, is understood to mean any complex containing a stress protein and a peptide that is capable of inducing an immune response in a mammal. The peptides are preferably non covalently associated with the stress protein. The complexes may include, but are not limited to, Hsp60-peptide, Hsp70-peptide and Hsp90-peptide complexes. In a preferred aspect of the invention a stress protein belonging to the Hsp90 family, namely gp96 can be used to generate an effective vaccine containing a gp96-peptide complex. Since the peptides can be dissociated from the complex in the presence of ATP or low pH potentially antigenic peptides can be isolated from cells infected with a preselected intracellular pathogen. Consequently, the antigenic determinants for potentially any intracellular pathogen of interest can be identified readily using the methodologies described herein.

The term "cytotoxic T cell", as used herein, is understood to mean any T lymphocyte expressing the cell surface glycoprotein marker CD8 that is capable of targeting and lysing a target cell which bears a class I histocompatibility complex on its cell surface and is infected with an intracellular pathogen. The term "cytotoxic T cell response" is understood to mean any cytotoxic activity that is mediated by cytotoxic T cells.

As used herein, the term "intracellular pathogen" is understood to mean any viable organism including, but not limited to, viruses, bacteria, fungi, protozoa and intracellular parasites, capable of existing within a mammalian cell and causing a disease in the mammal.

In a preferred aspect of the invention, the stress protein-peptide vaccines have particular utility in treating human diseases caused by intracellular pathogens. However, it is appreciated that the vaccines developed using the principles described herein will be useful in treating diseases of other mammals, for example, farm animals including: cattle; horses; goats; sheep; pigs; etc. and household pets including: cats; dogs; etc.

Vaccines may be prepared that stimulate cytotoxic T cell responses against cells infected with viruses including, but not limited to, hepatitis type A, hepatitis type B, hepatitis type C, influenza, varicella, adenovirus, herpes simplex type I (HSV-I), herpes simplex type II (HSV-II), rinderpest, rhinovirous, echovirus, rotavirus, respiratory syncytial virus, papilloma virus, papova virus, cytomegalovirus, echinovirus, arbovirus, huntavirus, coxsackie virus, mumps virus, measles virus, rubella virus, polio virus, human immunodeficiency virus type I (HIV-I), and human immunodeficiency virus type II (HIV-II). Vaccines also may be prepared that stimulate cytotoxic T cell responses against cells infected with intracellular bacteria, including, but not limited to, mycobacteria, rickettsia, mycoplasma, neisseria and legionella. Vaccines also may be prepared that stimulate cytotoxic T cell responses against cells infected with intracellular protozoa, including, but not limited to, leishmania, kokzidioa, and trypanosoma. Vaccines may be prepared that stimulate cytotoxic T cell responses against cells infected with intracellular parasites including, but not limited to, chlamydia and rickettsia.

In another preferred embodiment of the invention, the stress protein-peptide vaccine may also contain a therapeutically active amount of a cytokine. As used herein, the term "cytokine" is meant to mean any secreted polypeptide that influences the function of other cells mediating an immune response. Currently, preferred cytokines include: interleukin-1α (IL-1α), interleukin-1β (IL-1β), interleukin-2 (IL-2), interleukin-3 (IL-3), interleukin-4 (IL-4), interleukin-5 (IL-5), interleukin-6 (IL-6), interleukin-7 (IL-7), interleukin-8 (IL-8), interleukin-9 (IL-9), interleukin-10 (IL-10), interleukin-11 (IL-11), interleukin-12 (IL-12), interferon α (IFNα), interferon β (IFNβ), interferon γ (IFNγ), tumor necrosis factor α (TNFα), tumor necrosis factor β (TNFβ), granulocyte colony stimulating factor (G-CSF), granulocyte/macrophage colony stimulating factor (GM-CSF), and transforming growth factor β (TGF-β). However, it is contemplated that other but as yet undiscovered cytokines may be effective in the invention. In addition, conventional antibiotics may be coadministered with the stress protein-peptide complex. The choice of suitable antibiotics will however be dependent upon the disease in question.

It has been discovered that the vaccine stimulates the cytotoxic T cell response via the major histocompatibility complex (MHC) class I cascade. Thus it is contemplated that the cytotoxic T cell response may be further enhanced by coadministering the vaccine with a therapeutically amount of one or more of the cytokines disclosed hereinabove.

Another preferred embodiment, the invention provides a method for stimulating in a mammal a cellular immune response, specifically a cytotoxic T cell response, against cells infected with a preselected intracellular pathogen. The method involves administering to the mammal a vaccine made in accordance with the principles disclosed herein in an amount sufficient to elicit in the mammal a cytotoxic T cell response against the preselected intracellular pathogen.

The vaccine may be administered prophylactically to a mammal in order to stimulate in the mammal a cytotoxic T cell response that prevents subsequent infection of the mammal by the intracellular pathogen. Alternatively, the vaccine may be administered therapeutically to a mammal having a disease caused by an intracellular pathogen. It is contemplated that the vaccine may stimulate a cytotoxic T cell response against cells presently infected with the intracellular pathogen.

The dosage and means of administration of the family of stress protein-peptide vaccines will necessarily depend upon the nature of the complex, the intracellular pathogen and the nature of the disease in question. The complex should be administered in an amount sufficient to initiate a cytotoxic T cell response against the intracellular pathogen. In general, the amount of stress protein-peptide complex administered may be about 1–1000 micrograms of complex/kg body weight of the mammal/immunization, preferably 100–250 micrograms of complex/kg body weight of the mammal/ immunization, and in particular, about 7.5 to about 18.75 mg for a human subject weighing about 75 kg. The recipient should preferably be vaccinated three times at two week intervals. If necessary, the responses may be boosted at a later date by subsequent administration of the vaccine. It is contemplated that the optimal dosage and vaccination schedule may be determined empirically for each stress protein-peptide vaccine complex by an artisan using techniques well known in the art.

In another preferred embodiment, the invention provides a variety of methodologies for preparing commercially available amounts of the stress-protein peptide vaccines which when administered to a mammal induce in the mammal a cytotoxic T cell response against cells infected with a preselected antigen. In one approach, the stress protein-peptide complex may be harvested from any sample of tissue, isolated cell or immortalized cell line infected with the preselected intracellular pathogen using conventional protein purification methodologies. The purified complex subsequently may be stored or combined with a pharmaceutically acceptable carrier for administration as a vaccine.

Alternatively, the stress protein-peptide complex may be prepared by reconstituting a potentially antigenic peptide and a stress protein in vitro. For example, the antigenic peptide may be eluted from either a purified stress protein-peptide complex or a MHC-peptide complex using methodologies known in the art. Specifically, the peptides may be eluted from the stress protein-peptide complex by incubating the complex in the presence of ATP or low pH. Alternatively, the peptides may be eluted from the MHC-peptide complex by incubating the complex in the presence of trifluoroacetic acid (TFA). The resulting peptides may be purified by reverse phase HPLC and their amino acid sequences determined by standard protein sequencing methodologies. Peptides of defined sequence then may be synthesized using conventional peptide synthesis or other methodologies. Stress proteins may be purified directly from cells naturally expressing the stress proteins. Alternatively, recombinant stress proteins, including non native forms, truncated analogs, muteins, fusion proteins as well as other constructs capable of mimicking the peptide binding and immunogenic properties of stress proteins may be expressed using conventional recombinant DNA methodologies. For example, a recombinant stress protein may be expressed from recombinant DNA either in a eukaryotic or prokaryotic expression system and purified from the expression system. The two purified components may then be combined in vitro to generate a synthetic and completely defined stress protein-peptide complex. The immunogenicity and specificity of the recombinant complexes subsequently may be assayed in vitro and in vivo to identify useful candidate complexes that stimulate cytotoxic T cell responses against a preselected intracellular pathogen. Once identified, the synthetic complexes may be prepared on any scale, stored as is, or combined with pharmaceutically acceptable carriers for administration to mammals.

BRIEF DESCRIPTION OF THE DRAWINGS

The foregoing and other objects and features of the invention, as well as the invention itself, may be more fully understood from the following description, when read together with the accompanying drawings, in which.

(empty circles) and from the syngeneic non-NP transfected call line 5117 (asterisks).

Figure 2:
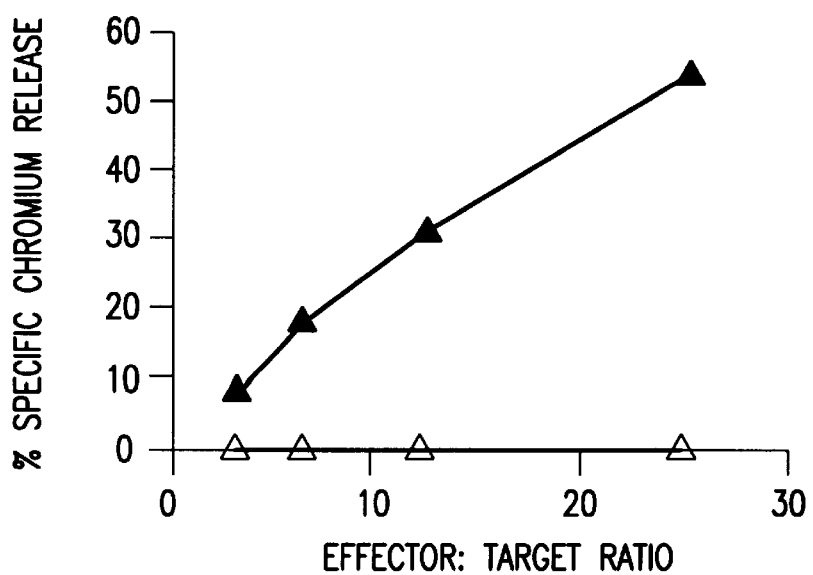
Figure 3A:
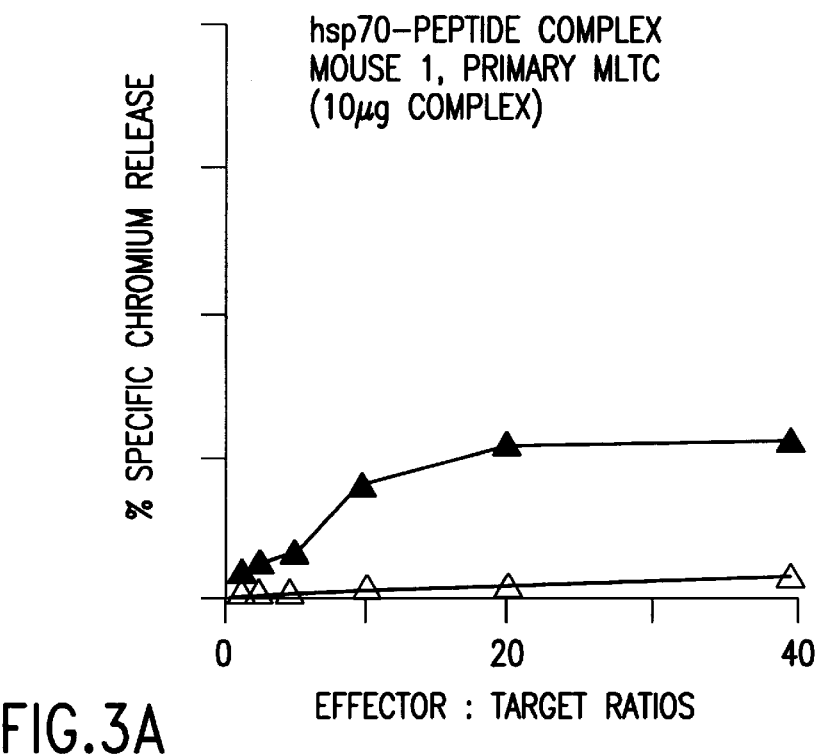
Figure 3B:
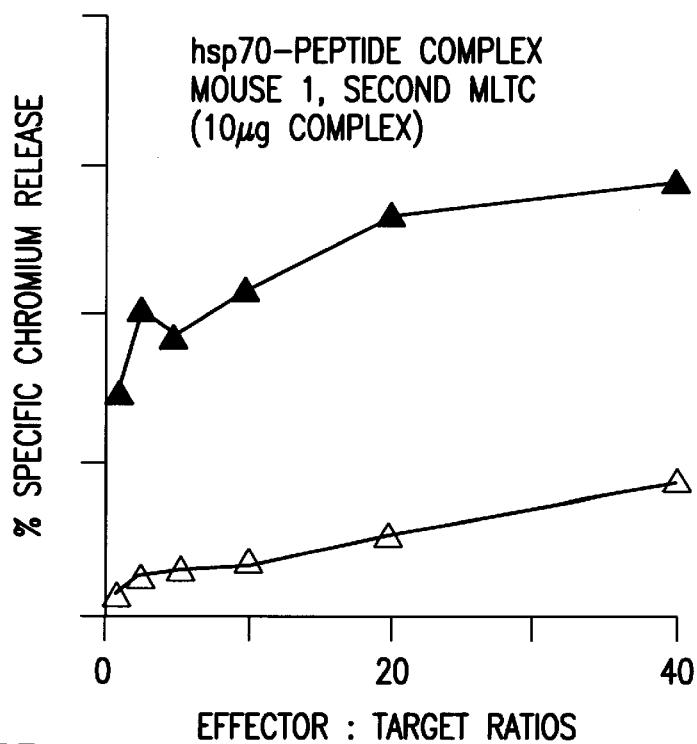
Figure 3C:
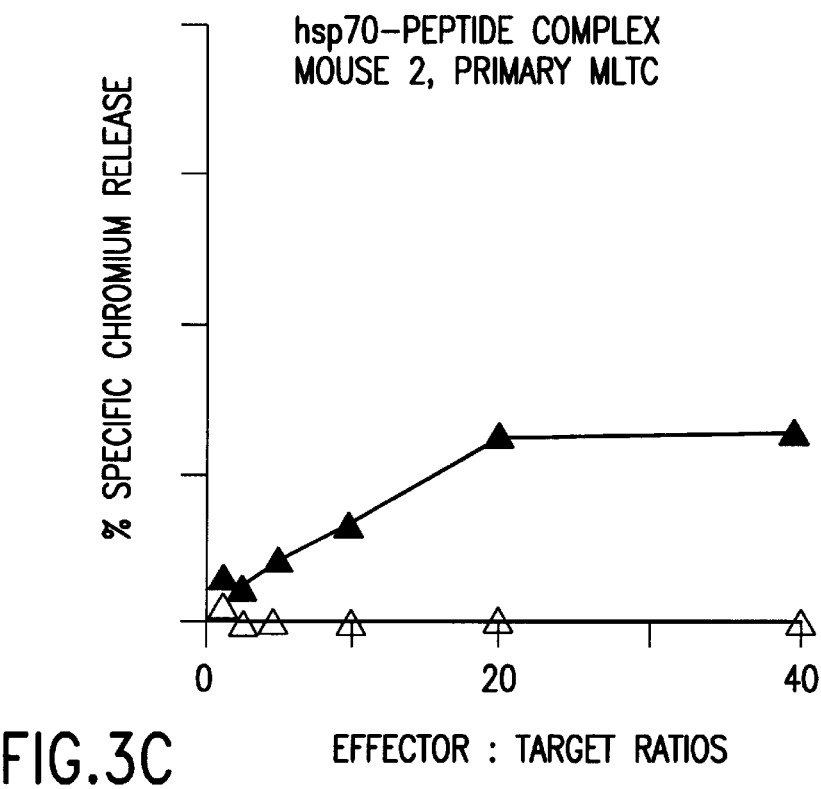
Figure 3D:
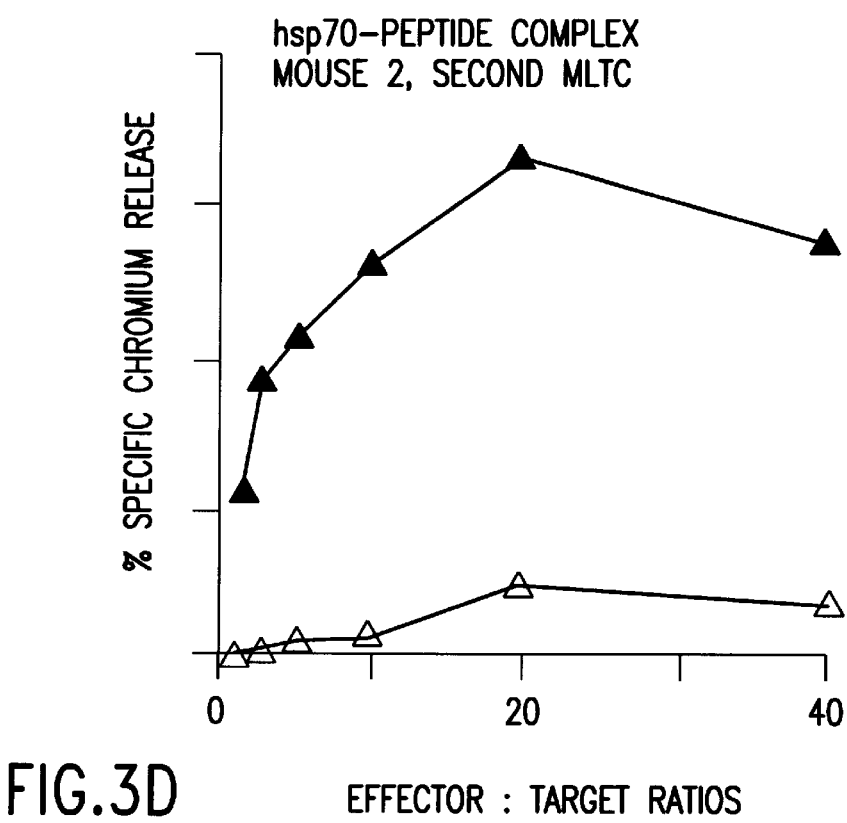

FIG. 2 shows antigen specific cytotoxic T cell activity of splenocytes derived from mice immunized with gp96-peptide complex harvested from SV40 transformed SVB6 cells. The cytotoxic activity was assayed by the release of $^{51}$Cr from SVB6 cells (filled circles) and from a non-SV40 transformed syngeneic cell line, MCA (empty circles).

FIG. 3A–3D shows antigen specific cytotoxic T cell activities of splenocytes derived from two mice immunized with a reconstituted Hsp70-peptide complex where the peptide has the sequence SLSDLRGYVYQGL (SEQ. ID. NO.:1). Prior to performing the assay, the splenocytes derived from each mouse were stimulated either once (3A and 3C) or twice (3B and 3D) in vitro with lethally irradiated cells transfected with, and expressing the peptide SLSDL-RGYVYQGL (SEQ. ID. NO.:1). Cytotoxic activity was assayed by the release of $^{51}$Cr from EL4 cells expressing the peptide (filled triangle) and from EL4 cells not expressing the peptide (empty triangles).

DETAILED DESCRIPTION

The invention is based on the discovery that a stress protein-peptide complex isolated from a eukaryotic cell infected with a preselected intracellular pathogen when administered to a mammal can stimulate a cytotoxic T cell response directed against cells infected with the same pathogen. This discovery provides a significant advance to the field of vaccine development.

It is generally believed that cellular responses are required for immunizing mammals against intracellular pathogens. See for example, "Advanced Immunology," Male et al. (1991) Gower Medical Publishing. Specifically, it is believed that the stimulation of a cytotoxic T cell response is critical for providing immunity to infections caused by intracellular pathogens. However, since subunit and inactivated whole organism vaccines tend not to stimulate cytotoxic T cell responses [Lussow et al. (1991) Eur. J. Immunol. 21:2297–2302; Barrios et al. (1992) Eur. J. Immunol. 22:1365–1372; and Raychaudhuri et al. (1993) Immunol. Today 14;344–348] conventional subunit and inactivated whole organism vaccines tend to be ineffective at vaccinating a recipient against intracellular pathogens.

In accordance with the invention, the aforementioned discovery is exploited to provide a family of vaccines which may be used to immunize mammals against diseases caused by intracellular pathogens. In essence, the vaccines can be prepared against any intracellular pathogen of interest, for example: viruses; bacteria; protozoa; fungi; or intracellular parasites. Generic methodologies useful for preparing vaccines against all of these classes of pathogens are discussed in detail hereinafter.

As will be appreciated by those skilled in the art, the stress protein-peptide vaccines described herein have several advantages over the vaccines currently available. First, the stress protein-peptide vaccines provide an alternative approach for stimulating cellular immunity and obviate the use of intact intracellular (attenuated or otherwise) pathogens. Secondly, since the vaccines do not contain intact organisms there is no risk of causing the disease the vaccine was designed to induce immunity against. Thirdly, the vaccines described herein are ideal for inducing immune responses against intracellular pathogens having undefined antigenic determinants or having constantly changing antigenic determinants. Accordingly, vaccines may be prepared that are effective against pathogens that normally evade the immune system by evolving new antigenic coat proteins, i.e., the influenza virus. Fourthly, vaccines of this type may in principle be prepared against any intracellular pathogen of interest. Fifthly, the vaccines may be prepared synthetically using the methodologies described hereinafter thereby providing completely defined vaccines that are suitable for administration to humans.

It is contemplated that the vaccines may be administered either prophylactically or therapeutically. When administered prophylactically the vaccine may stimulate in the mammal a cytotoxic T cell response that permits the vaccinee to resist subsequent infection by the intracellular pathogen. Alternatively, when administered therapeutically the vaccine may stimulate in the mammal a cytotoxic T cell response against a pathogen which is presently infecting and causing disease in the mammal.

The specific component of the vaccine that induces in the recipient a specific cytotoxic T cell response against the pathogen is a stress protein-peptide complex. The peptide may be any amino acid sequence that is present in a eukaryotic cell infected with an intracellular pathogen but not present when the cell is not infected with the same pathogen. This includes peptides that not only originate from the pathogen itself but also are synthesized by the infected cell in response to infection by the intracellular pathogen.

The immunogenic complexes may be purified from any eukaryotic cells, including: whole tissues; isolated cells; and immortalized eukaryotic cell lines infected with the intracellular pathogen. The complexes may be purified by using conventional protein purification techniques well known in the art. For example, it is contemplated that an immunogenic complex capable of stimulating a cytotoxic T cell response against the influenza virus may be harvested from a eukaryotic cell line that is infected with the influenza virus.

In addition in has been found that the peptide can be eluted from the stress protein-complex either in the presence of ATP or low pH. Neither the peptide nor the stress protein individually are effective at inducing a cytotoxic T cell response. However, these experimental conditions may be used to isolate peptides from infected cells which may contain potentially useful antigenic determinants. Once isolated the amino acid sequence of each antigenic peptide may be determined using conventional amino acid sequencing methodologies. Consequently, the antigenic determinants for potentially any intracellular pathogen of interest can be identified readily using the methodologies described herein. As discussed in detail hereinafter, this property may be exploited in the preparation of completely synthetic vaccines.

Similarly, it has been found that potentially immunogenic peptides may be eluted from MHC-peptide complexes using techniques well known in the art. See for example, Falk et al. (1990) Nature 348:248–251; Rotzsche et al. (1990) Nature 348:252–254; Elliott et al. (1990) Nature 348:195–197; Falk et al. (1991) Nature 351:290–296, Demotz et al. (1989) Nature 343:682–684; Rotzsche et al. (1990) Science 249:283–287, the disclosures of which are incorporated herein by reference. Although the peptides eluted from the MHC complexes may define a potentially protective antigenic determinant, it is appreciated that administration of the peptide in a conventional subunit vaccine may be ineffective at stimulating a cytotoxic T cell response in the recipient. Consequently, it is contemplated that the peptides eluted from MHC-peptide complexes may be reconstituted with a stress protein, using the methodologies described herein, thereby to generate a stress proteinpeptide complex effective at stimulating a cytotoxic T cell response capable of targeting and lysing cells expressing the antigenic peptide.

Stress proteins useful in the practice of the instant invention may be defined as any cellular protein that satisfies the following criteria. It is a protein whose intracellular concentration increases when a cell is exposed to a stressful stimuli, it is capable of binding other proteins or peptides, and it is capable of releasing the bound proteins or peptides in the presence of adenosine triphosphate (ATP) or low pH.

The first stress proteins to be identified were the heat shock proteins (Hsp). As their name implies, Hsps' are synthesized by a cell in response to heat shock. To date, three major families of Hsp have been identified based on molecular weight. The families have been called Hsp60, Hsp70 and Hsp90 where the numbers reflect the approximate molecular weight of the stress proteins in kilodaltons. Many members of these families were found subsequently to be induced in response to other stressful stimuli including, but not limited to, nutrient deprivation, metabolic disruption, oxygen radicals, and infection with intracellular pathogens. See for example: Welch (May 1993) *Scientific American* 56–64; Young (1990) *Annu. Rev. Immunol.* 8:401–420; Craig (1993) *Science* 260:1902–1903; Gething et al (1992) *Nature* 355:33–45; and Lindquist et al. (1988) *Annu. Rev. Genetics* 22:631–677, the disclosures of which are incorporated herein by reference. It is contemplated that stress proteins belonging to all of three families may be useful in the practice of the instant invention.

The major stress proteins can accumulate to very high levels in stressed cells, but they occur at low to moderate levels in cells that have not been stressed. For example, the highly inducible mammalian Hsp70 is hardly detectable at normal temperatures but becomes one of the most actively synthesized proteins in the cell upon heat shock [Welch et al. (1985), *J. Cell. Biol.* 101:1198–1211]. In contrast, Hsp90 and Hsp60 proteins are abundant at normal temperatures in most, but not all, mammalian cells and are further induced by heat [Lai et al. (1984), *Mol. Cell. Biol.* 4:2802–10; van Bergen en Henegouwen et al. (1987), *Genes Dev.*, 1:525–31].

Stress proteins are among the most highly conserved proteins in existence. For example, DnaK, the Hsp70 from *E. coli* has about 50% amino acid sequence identity with Hsp70 proteins from eukaryotes [Bardwell et al. (1984) *Proc. Natl. Acad. Sci.* 81:848–852]. The Hsp60 and Hsp90 families also show similarly high levels of intrafamilial conservation [Hickey et al. (1989) *Mol. Cell Biol.* 9:2615–2626; Jindal (1989) *Mol. Cell. Biol.* 9:2279–2283]. In addition, it has been discovered that the Hsp60, Hsp70 and Hsp90 families are composed of proteins that are related to the stress proteins in sequence, for example, having greater than 35% amino acid identity, but whose expression levels are not altered by stress. Therefore it is contemplated that the definition of stress protein, as used herein, embraces other proteins, muteins, analogs, and variants thereof having at least 35% to 55%, preferably 55% to 75%, and most preferably 75% to 85% amino acid identity with members of the three families whose expression levels in a cell are enhanced in response to a stressful stimulus. The purification of stress proteins belonging to these three families is described below.

The immunogenic stress protein-peptide complexes of the invention may include any complex containing a stress protein and a peptide that is capable of inducing an immune response in a mammal. The peptides are preferably non covalently associated with the stress protein. Preferred complexes may include, but are not limited to, Hsp60-peptide, Hsp70-peptide and Hsp90-peptide complexes. For example, a stress protein called gp96 which is present in the endoplasmic reticulum of eukaryotic cells and is related to the cytoplasmic Hsp90s' can be used to generate an effective vaccine containing a gp96-peptide complex.

Another family of low molecular weight heat shock proteins has now been identified and is called Hsp25–Hsp27. The purification of these proteins is discussed below. It is contemplated that these low molecular weight proteins may also have utility in the instant invention.

It has been discovered also that the stress protein-peptide complexes of the invention can be prepared from cells infected with an intracellular pathogen as well as cells that have been transformed by an intracellular pathogen. For example, immunogenic stress protein peptide-complexes may be isolated from eukaryotic cells transformed with a transforming virus such as SV40, see below.

In a preferred aspect of the invention, the purified stress protein-peptide vaccines may have particular utility in the treatment of human diseases caused by intracellular pathogens. However, it is appreciated that the vaccines developed using the principles described herein will be useful in treating diseases of other mammals, for example, farm animals including: cattle; horses; sheep; goats; pigs; etc., and household pets including: cats; dogs; etc., that are caused by intracellular pathogens.

In accordance with the methods described herein, vaccines may be prepared that stimulate cytotoxic T cell responses against cells infected with viruses including, but not limited to, hepatitis type A, hepatitis type B, hepatitis type C, influenza, varicella, adenovirus, herpes simplex type I (HSV-I), herpes simplex type II (HSV-II), rinderpest rhinovirous, echovirus, rotavirus, respiratory syncytial virus, papilloma virus, papova virus, cytomegalovirus, echinovirus, arbovirus, huntavirus, coxsackie virus, mumps virus, measles virus, rubella virus, polio virus, human immunodeficiency virus type I (HIV-I), and human immunodeficiency virus type II (HIV-II). Similarly, vaccines may also be prepared that stimulate cytotoxic T cell responses against cells infected with intracellular bacteria, including, but not limited to, mycobacteria, rickettsia, mycoplasma, neisseria and legionella. In addition, vaccines may also be prepared that stimulate cytotoxic T cell responses against cells infected with intracellular protozoa, including, but not limited to, leishmania, kokzidioa, and trypanosoma. Furthermore, vaccines may be prepared that stimulate cytotoxic T cell responses against cells infected with intracellular parasites including, but not limited to, chlamydia and rickettsia.

Propagation of Infected Eukaryotic Cells

As will be appreciated by those skilled in the art, the protocols described herein may be used to isolate stress protein-peptide complexes from any eukaryotic cell, for example, tissues, isolated cells or immortalized eukaryotic cell lines infected with a preselected intracellular pathogen.

When immortalized animal cell lines are used as a source of the stress protein-peptide complex it is of course important to use cell lines that can be infected with the pathogen of interest. In addition, it is preferable to use cells that are derived from the same species as the intended recipient of the vaccine.

For example, in order to prepare a stress protein-peptide complex for administration to humans that may be effective against HIV-I, the virus may be propagated in human cells which include, but are not limited to, human CD4+ T cells, HepG2 cells, and U937 promonocytic cells. In order to prepare a stress protein-peptide complex for administration to humans that may be effective against HIV-II, the virus may be propagated in human CD4+ T cells. Similarly, influenza viruses may be propagated in human fibroblast cell lines and MDCK cells. In addition, mycobacteria may be cultured in human Schwaan cells.

If the intracellular pathogens do not lyse the infected cells then the infected cells are cultured under the same conditions as the normal uninfected cells. For example, mycobacteria may be propagated in nerve cultures of the sensory ganglia of newborn Swiss white mice. The nerve cells are cultured in a growth medium containing 70% Dulbecco modified Eagle minimal essential medium (DMEM) with 0.006% glucose, 20% fetal calf serum, 10% chicken embryo extract and cytosine arabinoside. After eight to ten days, the cultures are inoculated with 5–8×10$^6$ mycobacteria isolated from fresh nodules of untreated lepromatous leprosy patients. The infected cells may be cultured at 37° C., for up to 6 weeks, after which the the infected cells are harvested and the stress protein-peptide complexes isolated. See for example, Mukherjee et al. (1985) *J. Clin. Micro.* 21:808–814, the disclosure of which is incorporated herein by reference.

If, on the other hand, the host cells are lysed by the pathogen of interest (as in the case of influenza viruses) the cells may still grown under standard conditions except the cells are washed and harvested just prior to lysis of the host cell. For example, during the purification of stress protein-peptide complexes from influenza infected cells, fibroblasts (or other cell types) are infected for 1 hour at 37° C. with 5–10 plaque forming units (PFU) of virus per cell. The infected cells may be cultured in plain DMEM medium for 24 hours at 37° C. After 24 hours the cells are washed and harvested prior to lysis. The stress protein-peptide complexes may be isolated using the procedures set forth below.

In addition, when the gene encoding a particular antigenic determinant has been identified, the gene of interest may be transfected and expressed in an immortalized human or other mammalian cell line using techniques well known in the art. See for example "*Current Protocols in Molecular Biology*" (1989), eds. Ausubel F M, Brent R, Kingston R E, Moore D D, Seidman J G, Smith J A and Struhl K, Wiley Interscience, the disclosure of which is incorporated by reference herein. The transfected cells may be grown under standard conditions and the complexes isolated subsequently.

Preparation of Stress Proteins and Immunogenic Stress Protein-Peptide Complexes Purification of Hsp70-peptide complexes.

A pellet of infected cells is resuspended in 3 volumes of 1X Lysis buffer consisting of 5 mM sodium phosphate buffer (pH7), 150 mM NaCl, 2 mM $CaCl_2$, 2 mM $MgCl_2$ and 1 mM phenyl methyl sulfonyl fluoride (PMSF). The pellet is sonicated, on ice, until >99% cells are lysed as judged by microscopic examination. Alternatively, the cells may be lysed by mechanical shearing. In this procedure, the cells are resuspended in 30 mM sodium bicarbonate pH 7.5, 1 mM PMSF, incubated on ice for 20 min and then homogenized in a dounce homogenizer until >95% cells are lysed.

The lysate is centrifuged at 1000 g for 10 minutes to remove unbroken cells, nuclei and other debris. The supernatant from this centrifugation step is then recentrifuged at 100,000 g for 90 minutes.

The supernatant is then applied to a Con A SEPHAROSE™ column, previously equilibrated with phosphate buffered saline (PBS) containing 2 mM each of $Ca^{2+}$ and $Mg^{2+}$. If the cells are lysed by mechanical shearing, the supernatant is diluted with an equal volume of 2X Lysis buffer before proceeding. The supernatant is mixed with the Con A SEPHAROSE™ and gently shaken at 4° C. for 2–3 hours. The material that does not bind is dialyzed for 36 hours (three times, 100 volumes each time) against 10 mM Tris-Acetate pH 7.5, 0.1 mM EDTA, 10 mM NaCl, 1 mM PMSF. The dialyzate is centrifuge centrifuge at 17,000 rpm (Sorvall SS34 rotor) for 20 min. The supernatant, is then applied to a MONO Q FPLC™ ion exchange chromatographic column (Pharmacia) equilibrated in 20 mM Tris-Acetate pH 7.5, 20 mM NaCl, 0.1 mM EDTA and 15 mM 2-mercaptoethanol. The proteins are then eluted by a 20 mM to 500 mM NaCl gradient. The fractions are characterized by sodium dodecyl sulfate-polyacrylamide gel electrophoresis (SDS-PAGE) and immunoblotting using an appropriate anti-Hsp70 antibody (from clone N27F3-4, from StressGen).

The fractions that are strongly immunoreactive with the antibody are pooled and the Hsp70-peptide complexes precipitated with ammonium sulfate. The complex is precipitated in the 50%–70% ammonium sulfate cut. The protein pellet is harvested by centrifugation at 17,000 rpm (SS34 Sorval rotor) and washed with 70% ammonium sulfate. The pellet is then solubilized and the residual ammonium sulfate removed by gel filtration on a SEPHADEX™ G25 column (Pharmacia).

The Hsp70-peptide complex can be purified to apparent homogeneity using this method. Up to 1 mg of Hsp70-peptide complex can be purified from 1 g of cells/tissue.

Purification of Hsp70.

The Hsp70 polypeptide may be purified from the Hsp70-peptide complex by ATP agarose chromatography. See for example, Welch et al. (1985) *Mol. Cell. Biol.* 5:1229, the disclosure of which is incorporated herein by reference. $MgCl_2$ is added to the previously isolated complex to a final concentration of 3 mM. The complex is then applied to an ATP agarose column (Sigma Chemical Co.) equilibrated in 20 mM Tris-Acetate (pH 7.5), 20 mM NaCl, 0.1 mM EDTA, 15 mM 2-mercaptoethanol, 3 mM $MgCl_2$ The column is washed extensively with the equilibration buffer containing 0.5M NaCl, and then washed with buffer alone. The Hsp70 is then eluted from the column with equilibration buffer containing 3 mM ATP (A-5394 Sigma).

Purification of Hsp90-peptide complexes.

A pellet of infected cells is resuspended in 3 volumes of 1X Lysis buffer consisting of 5 mM sodium phosphate buffer (pH7), 150 mM NaCl, 2 mM $CaCl_2$, 2 mM $MgCl_2$ and 1 mM PMSF. The cell pellet is sonicated, on ice, until >95% cells are lysed as judged by microscopic examination. Alternatively, the cells may be lysed by mechanical shearing, as before.

The lysate is centrifuged at 1000 g for 10 minutes to remove unbroken cells, nuclei and other debris. The supernatant from this centrifugation step is then recentrifuged at 100,000 g for 90 minutes.

The supernatant is then applied to a Con A SEPHAROSE™ column, previously equilibrated with PBS containing 2 mM each of $Ca^{2+}$ and $Mg^{2+}$. When the cells are lysed by mechanical shearing, the supernatant is diluted with equal volume of 2X Lysis Buffer before proceeding. The supernatant is mixed with the Con A SEPHAROSE™ and gently shaken at 4° C. for 2–3 hours. The material that does not bind is dialyzed for 36 hours (three times, 100 volumes each time) against 20 mM sodium phosphate pH 7.4, 1 mM EDTA, 250 mM NaCl, 1 mM PMSF. The dialyzate is centrifuged at 17,000 rpm (Sorvall SS34 rotor) for 20 min. The supernatant, is then applied to a MONO Q FPLC™ ion exchange chromatographic column (Pharmacia) equilibrated with lysis buffer. The proteins are then eluted with a a salt gradient of 200 mM to 600 mM NaCl.

The eluted fractions are analyzed by SDS-PAGE the Hsp90 complexes identified by immunoblotting using a anti-Hsp90 antibody such as 3G3 (Affinity Bioreagents). Hsp90 can be purified to apparent homogeneity using this procedure. Approximately 150–200 µg of Hsp90 can be routinely purified from 1 g of cells/tissue.

Purification of gp96-peptide complexes.

A pellet of infected cells is resuspended in 3 volumes of 1X Lysis buffer consisting of 5 mM sodium phosphate buffer (pH7), 150 mM NaCl, 2 mM $CaCl_2$, 2 mM $MgCl_2$ and 1 mM PMSF. The cell pellet is sonicated, on ice, until >95% cells are lysed as judged by microscopic examination. Alternatively, the cells may be lysed by mechanical shearing, as before.

The lysate is centrifuged at 1000 g for 10 minutes to remove unbroken cells, nuclei and other debris. The supernatant from this centrifugation step is then recentrifuged at 100,000 g for 90 minutes. The gp96-peptide complex can be purified either from the 100,000 g pellet or the supernatant.

When purified from the supernatant, the supernatant is applied to a Con A SEPHAROSE™ column equilibrated with PBS containing 2 mM $Ca^{2+}$ and 2 mM $Mg^{2+}$. When the cells are lysed by mechanical shearing, the supernatant is diluted with equal volume of 2X Lysis Buffer before proceeding. The supernatant is mixed with the Con A Sepharose and gently shaken at 4° C. for 2–3 hours. The slurry is then packed into a column and washed with 1X lysis buffer until the $OD_{280}$ drops to baseline. The column is then washed with ½ column bed volume of 10% α-methyl mannoside (α-MM). The column is then sealed with a piece of parafilm and incubated at 37° C. for 15 min. The column is then cooled to room temperature and parafilm removed from the bottom of the column. Five column volumes of a α-MM is applied to the column and the eluate analyzed by SDS-PAGE. This material can be between 60 and 95% pure gp96, depending upon the cell type and the tissue-to-lysis buffer ratio used.

If further purification is required, the sample can be applied to a MONO Q FPLC™ ion exchange chromatographic column (Pharmacia) equilibrated with a buffer containing 5 mM sodium phosphate, pH7. The proteins are then eluted from the column with a 0–1M NaCl gradient. The gp96 fraction elutes between 400 mM and 550 mM NaCl.

Alternatively, when the gp96 fraction is isolated from the 100,000 g pellet, the pellet is suspended in 5 volumes of PBS containing 1% sodium deoxycholate without calcium and magnesium and incubated on ice for 1 h. The suspension is centrifuged at 20,000 g for 30 min and the supernatant dialyzed against several changes of PBS (without calcium and magnesium) to remove the detergent. The dialysate is centrifuged at 100,000 g for 90 min and the supernatant purified further. Calcium and magnesium are then both added to the supernatant to final concentrations of 2 mM. The sample is then applied to a MONO Q FPLC™ ion exchange chromatographic column (Pharmacia) equilibrated with a buffer containing 5 mM sodium phosphate, pH7. The proteins are then eluted from the column with a 0–1M NaCl gradient. The gp96 fraction elutes between 400 mM and 550 mM NaCl.

The gp96-peptide complexes can be purified to apparent homogeneity using this procedure. About 10–20 µg of gp96 can be isolated from 1 g cells/tissue.

Purification of HSP25 and HSP27.

The purification of Hsp25 and Hsp27 polypeptides has been disclosed previously and so is not discussed in detail herein. See for example Jakob et al. (1993) *J. Biol. Chem.* 268:1517–1520, the disclosure of which is incorporated herein by reference.

Briefly, the cell lysates are precipitated with 35% ammonium sulfate. The pellet is harvested by centrifugation, solubilized in buffer and fractionated by ion exchange chromatography using a DEAE SEPHAROSE™ CL-6B column (Pharmacia Biotechnolgy, Inc.). The proteins are eluted with 50–200 mM NaCl gradient. The fractions containing Hsp25 and Hsp27 are identified by immunoblotting using suitable antibodies. The fractions are combined and fractionated by size exclusion chromatography on a SUPEROSE™ 6 gel filtration column (Pharmacia).

Purification of Hsp60.

The purification of Hsp60 has been discussed in detail previously and so is not discussed in detail herein. See for example, Vitanen et al. (1992) *J. Biol. Chem.* 267: 695–698, the disclosure of which is incorporated herein by reference.

Briefly, a mitochondrial matrix lysate is applied to a MONO Q FPLC™ ion exchange chromatographic column (Pharmacia) equilibrated with 50 mM sodium phosphate, 1 mM $MgCl_2$, 1 mM EGTA, pH 6.9. The proteins are eluted with a 0–1M NaCl gradient. The fractions containing Hsp65 are pooled and fractionated by ATP agarose chromatography as discussed above.

Preparation of Recombinant Stress Proteins

It is also appreciated that recombinant stress proteins and their sequence variants may be prepared using conventional recombinant DNA methodologies. For example, recombinant DNAs encoding either a known stress protein or its homologues can be inserted into a suitable host cell, the protein expressed, harvested, renatured if necessary, and purified. Stress proteins currently known in the art are summarized in Table I, below.

The processes for manipulating, amplifying, and recombining DNA which encode amino acid sequences of interest are generally well known in the art, and therefore, not described in detail herein. Methods of identifying and isolating genes encoding members of the stress protein families also are well understood, and are described in the patent and other literature.

TABLE I

Families of Stress Proteins
from Gething et al., Infra

| Organism/ Organelle | Hsp 60 | Hsp 70 | Hsp 90 |
|---|---|---|---|
| *E. coli* | GroEL | DnaK | HtpG (C62.5) |
| Yeast | | | |
| /cytosol | | Ssal-4p | Hsp 83/Hsc83 |
| /endoplasmic reticulum | | Kar2p (BiP) | |
| /mitochondria | Hsp 60 (Mif4p) | Ssclp | |
| Drosophila | | | |
| | | Hsp 68 | |
| | | Hsp 70 | |
| | | Hsc 1.2.4 | |

TABLE I-continued

Families of Stress Proteins
from Gething et al., Infra

| Organism/Organelle | Hsp 60 | Hsp 70 | Hsp 90 |
|---|---|---|---|
| Mammals | | | |
| /cytosol | | Hsp 70 (p73)<br>Hsc 70 (p72) | Hsp 90 (Hsp83)<br>Hsp 87 |
| /endoplasmic reticulum | | BiP (Grp 78) | Grp 94 (ERp99)<br>gp96 |
| /mitochondria | Hsp 60 (Hsp 58) | Hsp 70 (Grp 75) | |
| Plants | | | |
| /endoplasmic reticulum | | b70 (BiP) | |
| /chloroplasts | RUSBP | | |

Alternative names are shown in parentheses.

Accordingly, the construction of DNAS encoding biosynthetic constructs as disclosed herein can be performed using known techniques involving the use of various restriction enzymes which make sequence specific cuts in DNA to produce blunt ends or cohesive ends, DNA ligases, techniques enabling enzymatic addition of sticky ends to blunt-ended DNA, construction of synthetic DNAs by assembly of short or medium length oligonucleotides, CDNA synthesis techniques, and synthetic probes for isolating genes of members of the stress protein families. Various promoter sequences and other regulatory DNA sequences used in achieving expression, and various types of host cells are also known and available. Conventional transfection techniques, and equally conventional techniques for cloning and subcloning DNA are useful in the practice of this invention and known to those skilled in the art. Various types of vectors may be used such as plasmids and viruses including animal viruses and bacteriophages. The vectors may exploit various marker genes which impart to a successfully transfected cell a detectable phenotypic property that can be used to identify which of a family of clones has successfully incorporated the recombinant DNA of the vector.

DNA molecules encoding potentially useful stress proteins may be obtained by a variety of methods. Genes of interest may be purified from standard cDNA libraries using colony or plaque hybridization technologies or by using polymerase chain reaction (PCR) methodologies, all of which are well known in the art. See for example, "Molecular Cloning: A Laboratory Manual, 2nd Edition" Sambrook et al. (1989), Cold Spring Harbor Press, the disclosure of which is incorporated herein by reference. Alternatively, the preferred genes can be generated by the assembly of synthetic oligonucleotides produced in a conventional, automated, polynucleotide synthesizer followed by ligation with appropriate ligases. For example, overlapping, complementary DNA fragments comprising 15 bases may be synthesized semi manually using phosphoramidite chemistry, with end segments left unphosphorylated to prevent polymerization during ligation. One end of the synthetic DNA is left with a "sticky end" corresponding to the site of action of a particular restriction endonuclease, and the other end is left with an end corresponding to the site of action of another restriction endonuclease. Alternatively, this approach can be fully automated. The DNA encoding the biosynthetic constructs may be created by synthesizing longer single strand fragments (e.g., 50–100 nucleotides long) in, for example, a Biosearch oligonucleotide synthesizer, and then ligating the fragments.

The recombinant DNA constructs then may be integrated into an expression vector and transfected into an appropriate host cell for protein expression. Useful host cells include E. coli, Saccharomyces, the insect/baculovirus cell system, myeloma cells, and various other mammalian cells. In E. coli and other microbial hosts, the synthetic genes can be expressed as fusion proteins. Expression in eukaryotes can be accomplished by the transfection of DNA sequences encoding the biosynthetic protein of interest into myeloma or other type of cell line.

The vector additionally may include various sequences to promote correct expression of the recombinant protein, including transcriptional promoter and termination sequences, enhancer sequences, preferred ribosome binding site sequences, preferred mRNA leader sequences, preferred protein processing sequences, preferred signal sequences for protein secretion, and the like. The DNA sequence encoding the gene of interest also may be manipulated to remove potentially inhibiting sequences or to minimize unwanted secondary structure formation. The recombinant protein also may be expressed as a fusion protein. After being translated, the protein may be purified from the cells themselves or recovered from the culture medium.

For example, if the gene is to be expressed in E. coli, it may first be cloned into an expression vector. This is accomplished by positioning the engineered gene downstream of a promoter sequence such as Trp or Tac, and a gene coding for a leader peptide such as fragment B of protein A (FB). The resulting fusion proteins accumulate in refractile bodies in the cytoplasm of the cells, and may be harvested after disruption of the cells by French press or sonication. The refractile bodies are solubilized, and the expressed proteins refolded and cleaved by methods already established for many other recombinant proteins.

Expression of the engineered genes in eukaryotic cells requires the establishment of appropriate cells and cell lines that are easy to transfect, are capable of stably maintaining foreign DNA with an unrearranged sequence, and which have the necessary cellular components for efficient transcription, translation, post-translation modification, and secretion of the protein. In addition, a suitable vector carrying the gene of interest also is necessary. DNA vector design for transfection into mammalian cells should include appropriate sequences to promote expression of the gene of interest as described supra, including appropriate transcription initiation, termination, and enhancer sequences, as well as sequences that enhance translation efficiency, such as the Kozak consensus sequence. Preferred DNA vectors also include a marker gene and means for amplifying the copy number of the gene of interest. A detailed review of the state of the art of the production of foreign proteins in mammalian cells, including useful cells, protein expression-promoting sequences, marker genes, and gene amplification methods, is disclosed in Bendig, Mary M., *Genetic Engineering* 7:91–127 (1988).

The best characterized transcription promoters useful for expressing a foreign gene in a particular mammalian cell are the SV40 early promoter, the adenovirus promoter (AdMLP), the mouse metallothionein-I promoter (mMT-I), the Rous sarcoma virus (RSV) long terminal repeat (LTR), the mouse mammary tumor virus long terminal repeat (MMTV-LTR), and the human cytomegalovirus major intermediate-early promoter (hCMV). The DNA sequences for all of these promoters are known in the art and are available commercially.

The use of a selectable DHFR gene in a dhfr- cell line is a well characterized method useful in the amplification of genes in mammalian cell systems. Briefly, the DHFR gene is provided on the vector carrying the gene of interest, and addition of increasing concentrations of the cytotoxic drug methotrexate leads to amplification of the DHFR gene copy number, as well as that of the associated gene of interest. DHFR as a selectable, amplifiable marker gene in transfected Chinese hamster ovary cell lines (CHO cells) is particularly well characterized in the art. Other useful amplifiable marker genes include the adenosine deaminase (ADA) and glutamine synthetase (GS) genes.

The choice of cells/cell lines is also important and depends on the needs of the experimenter. Monkey kidney cells (COS) provide high levels of transient gene expression, providing a useful means for rapidly testing vector construction and the expression of cloned genes. COS cells are transfected with a simian virus 40 (SV40) vector carrying the gene of interest. The transfected COS cells eventually die, thus preventing the long term production of the desired protein product. However, transient expression does not require the time consuming process required for the development of a stable cell line.

Among established cell lines, CHO cells may be the best characterized to date. CHO cells are capable of expressing proteins from a broad range of cell types. The general applicability of CHO cells and its successful production for a wide variety of human proteins in unrelated cell types emphasizes the underlying similarity of all mammalian cells.

The various cells, cell lines and DNA sequences that can be used for mammalian cell expression of the recombinant stress protein constructs of the invention are well characterized in the art and are readily available. Other promoters, selectable markers, gene amplification methods and cells also may be used to express the proteins of this invention. Particular details of the transfection, expression, and purification of recombinant proteins are well documented in the art and are understood by those having ordinary skill in the art. Further details on the various technical aspects of each of the steps used in recombinant production of foreign genes in mammalian cell expression systems can be found in a number of texts and laboratory manuals in the art, such as, for example, F. M. Ausubel et al., ed., *Current Protocols in Molecular Biology*, John Wiley & Sons, New York, (1989)

Isolation of Potentially Immunogenic Peptides

As mentioned previously, potentially immunogenic peptides may be isolated from either stress protein-peptide complexes or MHC-peptide complexes. Protocols for isolating peptides from either of these complexes are set forth below.

I. Peptides from Stress Protein-peptide Complexes.

Two methods may be used to elute the peptide from a stress protein-peptide complex. One approach involves incubating the stress protein-peptide complex in the presence of ATP. The other approach involves incubating the complexes in a low pH buffer.

Briefly the complex of interest is centrifuged through a Centricon 10 assembly (Millipore) to remove any low molecular weight material loosely associated with the complex. The large molecular weight fraction may be removed and analyzed by SDS-PAGE while the low molecular weight may be analyzed by HPLC as described below. In the ATP incubation protocol, the stress protein-peptide complex in the large molecular weight fraction is incubated with 10 mM ATP for 30 minutes at room temperature. In the low pH protocol, acetic acid is added to the stress protein-peptide complex to give a final concentration of 10% (vol/vol) and the mixture incubated in a boiling water bath for 10 minutes. See for example, Van Bleek et al. (1990) *Nature* 348:213–216; and Li et al. (1993) *EMBO Journal* 12:3143–3151, the disclosures of which are incorporated herein by reference.

The resulting samples are centrifuged through an Centricon 10 assembly as mentioned previously. The high and low molecular weight fractions are recovered. The remaining large molecular weight stress proteinpeptide complexes can be reincubated with ATP or low pH to remove any remaining peptides.

The resulting lower molecular weight fractions are pooled, concentrated by evaporation and dissolved in 0.1% trifluoroacetic acid (TFA). The dissolved material is then fractionated by reverse phase high pressure liquid chromatography (HPLC), using for example a VYDAC™ C18 reverse phase column equilibrated with 0.1% TFA. The bound material is then eluted at a flow rate of about 0.8 ml/min by developing the column with a linear gradient of 0 to 80% acetonitrile in 0.1% TFA. The elution of the peptides can be monitored by $OD_{210}$ and the fractions containing the peptides collected.

II. Peptides from MHC-peptide Complexes.

The isolation of potentially immunogenic peptides from MHC molecules is well known in the art and so is not described in detail herein. See for example, Falk et al. (1990) *Nature* 348:248–251; Rotzsche et al. (1990) *Nature* 348:252–254; Elliott et al. (1990) *Nature* 348:195–197; Falk et al. (1991) *Nature* 351:290–296, Demotz et al. (1989) *Nature* 343:682–684; Rotzsche et al. (1990) *Science* 249:283–287, the disclosures of which are incorporated herein by reference.

Briefly, MHC-peptide complexes may be isolated by a conventional immunoaffinity procedure. The peptides then may be eluted from the MHC-peptide complex by incubating the complexes in the presence of about 0.1% TFA in acetonitrile. The eluted peptides may be fractionated and purified by reverse phase HPLC, as before.

The amino acid sequences of the eluted peptides may be determined either by manual or automated amino acid sequencing techniques well known in the art. Once the amino acid sequence of a potentially protective peptide has been determined the peptide may be synthesized in any desired amount using conventional peptide synthesis or other protocols well known in the art.

Synthesis of Potentially Useful Immunogenic Peptides

Peptides having the same amino acid sequence as those isolated above may be synthesized by solid-phase peptide synthesis using procedures similar to those described by Merrifield, (1963) *J. Am. Chem. Soc.*, 85:2149. During synthesis, N-α-protected amino acids having protected side chains are added stepwise to a growing polypeptide chain linked by its C-terminal end to an insoluble polymeric support i.e., polystyrene beads. The peptides are synthesized by linking an amino group of an N-α-deprotected amino acid to an a-carboxy group of an N-α-protected amino acid that has been activated by reacting it with a reagent such as dicyclohexylcarbodiimide. The attachment of a free amino group to the activated carboxyl leads to peptide bond formation. The most commonly used N-α-protecting groups include Boc which is acid labile and Fmoc which is base labile.

Briefly, the C-terminal N-α-protected amino acid is first attached to the polystyrene beads. The N-α-protecting group is then removed. The deprotected a amino group is coupled to the activated α-carboxylate group of the next N-α-protected amino acid. The process is repeated until the desired peptide is synthesized. The resulting peptides are then cleaved from the insoluble polymer support and the amino acid side chains deprotected. Longer peptides can be derived by condensation of protected peptide fragments. Details of appropriate chemistries, resins, protecting groups, protected amino acids and reagents are well known in the art and so are not discussed in detail herein. See for example, Atherton et al., *Solid Phase Peptide Synthesis: A Practical Approach*, IRL Press, (1989), and Bodanszky, *Peptide Chemistry, A Practical Textbook*, 2nd Ed, Springer-Berlog (1993), the disclosures of which are incorporated herein by reference.

Purification of the resulting peptides is accomplished using conventional procedures, such as preparative HPLC using gel permeation, partition and/or ion exchange chromatography. The choice of appropriate matrices and buffers are well known in the art and so are not described in detail herein.

Reconstitution of Stress Protein-peptide Complexes

As will be appreciated by those skilled in the art, the peptides either isolated by the aforementioned procedures or chemically synthesized may be reconstituted with a variety of naturally purified or recombinant stress proteins in vitro to generate immunogenic stress protein-peptide complexes. A preferred protocol for reconstituting a stress protein and a peptide in vitro is discussed below.

Prior to reconstitution the stress proteins are pretreated with ATP or low pH to remove any peptides that may be associated with the stress-protein of interest. When the ATP procedure is used, excess ATP is removed from the preparation by the addition of apyranase as discussed in Levy et al. [Levy et al. (1991) *Cell* 67:265–274, the disclosure of which is incorporated herein by reference]. When the low pH procedure is used the buffer is readjusted to neutral pH by the addition of pH modifying reagents.

The peptide (1 $\mu$g) and the pretreated stress protein (9 $\mu$g) are admixed to give an approximate molar ratio of 5 peptides:1 stress protein. Then, the mixture is incubated for 3 hours at room temperature in a binding buffer containing 20 mM sodium phosphate, pH 7.2, 350 mM NaCl, 3 mM $MgCl_2$, 1 mM PMSF. The preparations are centrifuged through Centricon 10 assembly (Millipore) to remove any unbound peptide. The association of the peptides with the stress proteins can be assayed by SDS-PAGE.

Following reconstitution, the candidate immunogenic stress protein-peptide complexes can be identified in vitro using for example the mixed lymphocyte target cell assay (MLTC) described below. Once potential immunogenic constructs have been isolated they can be characterized further in animal models using the preferred administration protocols and excipients discussed below.

Determination of Immunogenicity of Stress Protein-Peptide Complexes

The purified and reconstituted stress protein-peptide complexes can be assayed for immunogenicity using the mixed lymphocyte target culture assay (MLTC) well known in the art.

Briefly, mice are injected subcutaneously with the candidate stress protein-peptide complexes. Other mice are injected with either other stress protein peptide complexes or whole infected cells which act as positive controls for the assay. The mice are injected twice, 7–10 days apart. Ten days after the last immunization, the spleens are removed and the lymphocytes released. The released lymphocytes may be restimulated subsequently in vitro by the addition of dead cells that expressed the complex of interest.

For example, $8 \times 10^6$ immune spleen cells may be stimulated with $4 \times 10^4$ mitomycin C treated or γ-irradiated (5–10,000 rads) infected cells (or cells transfected with an appropriate gene, as the case may be) in 3 ml RPMI medium containing 10% fetal calf serum. In certain cases 33% secondary mixed lymphocyte culture supernatant may be included in the culture medium as a source of T cell growth factors. See for example, Glasebrook et al. (1980) *J. Exp. Med.* 151; 876. To test the primary cytotoxic T cell response after immunization, spleen cells may be cultured without stimulation. In some experiments spleen cells of the immunized mice may also be restimulated with antigenically distinct cells, to determine the specificity of the cytotoxic T cell response.

Six days later the cultures are tested for cytotoxicity in a 4 hour $^{51}$Cr-release assay. See for example, Palladino et al. (1987) *Cancer Res.* 47:5074–5079 and Blachere et al. (1993) *J. Immunotherapy* 14; 352–356, the disclosures of which are incorporated herein by reference. In this assay, the mixed lymphocyte culture is added to a target cell suspension to give different effector:target (E:T) ratios (usually 1:1 to 40:1). The target cells are prelabelled by incubating $1 \times 10^6$ target cells in culture medium containing 200 mCi $^{51}$Cr/ml for one hour at 37° C. The cells are washed three times following labelling. Each assay point (E:T ratio) is performed in triplicate and the appropriate controls incorporated to measure spontaneous $^{51}$Cr release (no lymphocytes added to assay) and 100% release (cells lysed with detergent). After incubating the cell mixtures for 4 hours, the cells are pelleted by centrifugation at 200 g for 5 minutes. The amount of $^{51}$Cr released into the supernatant is measured by a gamma counter. The percent cytotoxicity is measured as cpm in the test sample minus spontaneously released cpm divided by the total detergent released cpm minus spontaneously released cpm.

In order to block the MHC class I cascade a concentrated hybridoma supernatant derived from K-44 hybridoma cells (an anti-MHC class I hybridoma) is added to the test samples to a final concentration of 12.5%.

Formulation and Vaccination Regimes

Once candidate stress protein-peptide complexes have been identified they may be administered either to an animal model or to the intended recipient to stimulate cytotoxic T cell responses against the preselected intracellular pathogen. The stress protein-peptide complexes of the invention may be either stored or prepared for administration by mixing with physiologically acceptable carriers, excipients, or stabilizers. These materials should be non-toxic to the intended recipient at dosages and concentrations employed.

If the complex is water soluble then it may be formulated in an appropriate buffer, for example phosphate buffered saline (5 mM sodium phosphate, 150 mM NaCl, pH7.1) or other physiologically compatible solutions. Alternatively, if the resulting complex has poor solubility in aqueous solvents then it may be formulated with a non-ionic surfactant such as Tween, or polyethylene glycol.

Useful solutions for oral or parenteral administration may be prepared by any of the methods well known in the pharmaceutical art, described, for example, in *Remington's*

*Pharmaceutical Sciences*, (Gennaro, A., ed.), Mack Pub., 1990. Formulations may include, for example, polyalkylene glycols such as polyethylene glycol, oils of vegetable origin, hydrogenated naphthalenes, and the like. Formulations for direct administration, in particular, may include glycerol and other compositions of high viscosity. Biocompatible, preferably bioresorbable polymers, including, for example, hyaluronic acid, collagen, tricalcium phosphate, polybutyrate, polylactide, polyglycolide and lactide/glycolide copolymers, may be useful excipients to control the release of the stress protein-peptide complexes in vivo.

Formulations for inhalation administration may contain as excipients, for example, lactose. Aqueous solutions may contain, for example, polyoxyethylene-9-lauryl ether, glycocholate and deoxycholate. oily solutions may be useful administration in the form of nasal drops. Gels may be applied topically intranasally.

The compounds provided herein can be formulated into pharmaceutical compositions by admixture with pharmaceutically acceptable nontoxic excipients and carriers. In addition the formulations may optionally contain one or more adjuvants. Preferred adjuvants include, but are not limited to, pluronic tri-block copolymers, muramyl dipeptide and its derivatives, detoxified endotoxin, saponin and its derivatives such as QS-21 and liposomes. The present invention further envisages sustained release formulations in which the complex is released over an extended period of time.

The dosage and means of administration of the family of stress protein-peptide vaccines prepared in accordance with the invention will necessarily depend upon the nature of the complex, the intracellular pathogen and the nature of the disease in question. The complex should be administered in an amount sufficient to initiate a cytotoxic T cell response against the intracellular pathogen. The preferred dosage of drug to be administered also is likely to depend on such variables as the type of disease, the age, sex and weight of the intended recipient, the overall health status of the particular patient, the relative biological efficacy of the compound selected, the formulation of the compound, the presence and types of excipients in the formulation, and the route of administration.

In general terms, the compounds of this invention may be provided in an aqueous physiological buffer solution containing about 0.001 to 10% w/v compound for parenteral administration. Typical dose ranges are from about 1 to 1000 micrograms of complex/kg body weight of recipient/immunization; preferably 100–250 micrograms of complex/kg body weight of recipient/immunization; and in particular about 7.5 mg to 18.75 mg for a human subject weighing about 75 kg. These quantities may vary according to the adjuvant coadministered with the complex.

The vaccines may be administered using standard protocols which include, but are not limited to, intramuscular, subcutaneous, intradermal, intraperitoneal, intravenous, intravaginal, intrarectal, oral, sublingual, transcutaneous, and intranasal administration. Preferably the recipient should be vaccinated three times at two week intervals. If necessary, the responses may be boosted at a later date by subsequent administration of the vaccine. It is contemplated that the optimal dosage and vaccination schedule may be determined empirically for each stress protein-peptide vaccine using techniques well known in the art.

Various cytokines, antibiotics, and other bioactive agents also may be administered with the stress protein complexes. For example, various known cytokines, i.e., interleukin-1α (IL-1α), interleukin-1β (IL-1β), interleukin-2 (IL-2), interleukin-3 (IL-3), interleukin-4 (IL-4), interleukin-5 (IL-5), interleukin-6 (IL-6), interleukin-7 (IL-7), interleukin-8 (IL-8), interleukin-9 (IL-9), interleukin-10 (IL-10), interleukin-11 (IL-11), interleukin-12 (IL-12), interferon α (IFNα), interferon β (IFNβ), interferon γ (IFNγ), tumor necrosis factor a (TNF ), tumor necrosis factor β (TNFβ), granulocyte colony stimulating factor (G-CSF), granulocyte/macrophage colony stimulating factor (GM-CSF), and transforming growth factor β (TGF-β) may be coadministered with the complexes in order to maximize the physiological response. However, it is anticipated that other but as yet undiscovered cytokines may be effective in the invention. In addition, conventional antibiotics may be coadministered with the stress protein-peptide complex. The choice of suitable antibiotics will however be dependent upon the disease in question.

Example 1

Immunogenicity of Stress Protein-peptide Complexes Isolated from Cells Transfected with a Gene Encoding an Antigenic Determinant.

Figure 1:
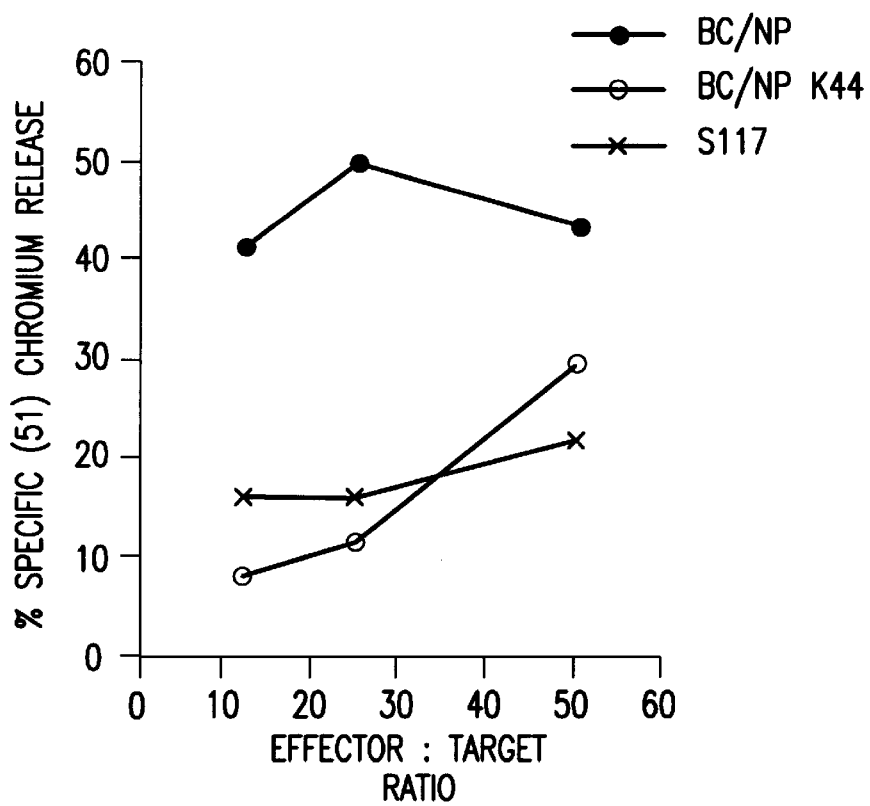
FIG. 1 shows antigen specific cytotoxic T cell activity of splenocytes derived from mice immunized with a gp96-peptide complex harvested from BALB/c fibroblasts transfected with the nucleoprotein (NP) gene from the PR8 influenza virus. The cytotoxic activity was assayed by the release of $^{51}$Cr from BALB/c fibroblasts expressing the NP gene (filled circles), BALB/c fibroblasts expressing the NP gene but treated with the anti-MHC type I antisera K44

FIG. 1 shows the antigen specific cytotoxic T cell activity of splenocytes derived from mice immunized with a gp96-peptide complex harvested from BALB/c fibroblasts transfected with the nucleoprotein (NP) gene from the PR8 influenza virus.

Briefly, gp96-peptide preparations were isolated from BALB/c cells transfected with and expressing the NP gene of the PR8 influenza virus. The preparations then were used to immunize naive BALB/c mice. The mice were injected twice sub-cutaneously with the gp96-peptide complexes at ten day intervals. The mice were sacrificed and the spleen cells obtained. The spleen cells were stimulated twice in vitro by the additional lethally irradiated BALB/c cells expressing the NP gene using the mixed target lymphocyte culture (MLTC) assay described above. Six days later the cultures were tested for cytotoxicity using the $^{51}$Cr release assay. In order to block the MHC type I cascade the spleen cells were incubated with the supernatant derived from K-44 hybridoma (containing anti-MHC type I immunoglobulins) culture.

The cytotoxic activity was assayed by the release of $^{51}$Cr from BALB/c fibroblasts expressing the NP gene (filled circles), BALB/c cells expressing the NP gene but treated with the anti-MHC type I antisera (empty circles) and from the syngeneic non-NP transfected cell line 5117 (asterisks). The spleens of the mice immunized with the gp96 complex showed strong MHC class I-restricted cytotoxic T cell activity against BALB/c cells expressing the NP gene, but not against the syngeneic non-NP transfected cell line 5117. Furthermore, the anti MHC type I antisera blocked the response. Therefore it is apparent that the MHC class I cascade plays an integral role in stimulating the cytotoxic T cell response against cells infected with intracellular pathogens.

Example 2

Immunogenicity of Stress Protein-peptide Complexes Isolated from Transformed Cells.

FIG. 2 shows the antigen specific cytotoxic T cell activity of splenocytes derived from mice immunized with the gp96-peptide complex harvested from SV40 transformed SVB6 cells.

Briefly, gp96-peptide complexes were isolated from SV40 transformed SVB6 cells and used to immunize naive (C57BL/6) mice. The mice were injected twice subcutaneously with the complex at ten day intervals. The mice were sacrificed, the spleen cells isolated and stimulated in vitro by the addition of lethally irradiated SV40 transformed SVB6 cells by the MLTC procedure, as described above. Six days later the cells were assayed for cytotoxicity using the $^{51}$Cr release assay. The cytotoxic activity was assayed by the release of $^{51}$Cr from SVB6 cells (filled triangles) and from a non SV40 transfected syngeneic cell line, MCA (empty triangles). MHC class I mediated activity was assayed also by adding anti-MHC class I immunoglobulins derived from the K44 hybridoma cell line to the spleen cells.

The spleen cells isolated from mice immunized with the gp96-peptide complex showed strong MHC class I-restricted activity against the SV40 transfected SVB6 cells but not against the non transfected cells.

SEQ. ID. NO.: 1, (filled triangles). The results show that stress proteins and peptides can be successfully reconstituted in vitro to give specific immunogenic stress proteinpeptide complexes.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
       (A) LENGTH: 13 amino acids
       (B) TYPE: amino acid
       (C) STRANDEDNESS: single
       (D) TOPOLOGY: linear (ii) MOLECULE TYPE: peptide (ix) FEATURE:
       (A) NAME/KEY: Peptide
       (B) LOCATION: 1..13
       (D) OTHER INFORMATION: /label= PEPTIDE1
           /note= "ANTIGENIC PEPTIDE I"

(xi) SEQUENCE DESCRIPTION: SEQ ID NO:1:

Ser Leu Ser Asp Leu Arg Gly Tyr Val Tyr Gln Gly Leu
1               5                   10

Example 3
Reconstitution of Immunogenic Stress Protein-peptide Complexes In Vitro.

FIGS. 3A–3D show antigen specific cytotoxic T cell activities of splenocytes derived from two mice immunized with a reconstituted Hsp70-peptide complex.

Briefly, Hsp70 was purified by the procedure described above and the peptide (SLSDLRGYVYQGL, SEQ. ID. NO.: 1) was synthesized by solid phase peptide synthesis. The peptide (1 μg) and ATP treated Hsp70 (9 μg) were admixed and incubated for 3 hours at room temperature in a binding buffer containing 20 mM sodium phosphate, pH 7.2, 350 mM NaCl, 3 mM MgCl$_2$, 1 mM PMSF. The resulting preparation was centrifuged through CENTRICON™ 10 assembly (Millipore) to remove any unbound peptide.

The resulting complex was used to immunize two naive mice. The spleen cells were isolated from the mice and stimulated twice in vitro by the addition of lethally irradiated EL4 cells transfected with, and expressing a minigene encoding the peptide SLSDLRGYVYQGL (SEQ. ID. NO.: 1), using the MLTC procedure. The cytotoxicities of spleen cells from both mice were assayed after the first (FIGS. 3A and 3C) and second (FIGS. 3B and 3D) stimulations by the $^{51}$Cr release assay. The release of $^{51}$Cr was measured from EL4 cells (hollow triangles) and from EL4 cells transfected with, and expressing the peptide SLSDLRGYVYQGL,

What is claimed is:

1. A composition comprising:
   (a) an amount of a purified population of immunogenic mammalian stress protein-peptide complexes sufficient to elicit in a mammal an immune response against an intracellular pathogen selected from the group consisting of a bacterium, protozoan, fungus and parasite, said population comprising a complex of
      a mammalian stress protein noncovalently associated with a peptide that is present in a eukaryotic cell infected with said pathogen but not present in said cell when said cell is not infected with said pathogen; and
   (b) a pharmaceutically acceptable carrier.

2. A composition comprising:
   a purified mammalian stress protein-peptide complex, said complex comprising
      a mammalian stress protein noncovalently associated with a peptide that is present in a eukaryotic cell infected with an intracellular pathogen selected from the group consisting of a bacterium, protozoan, fungus and parasite, but not present in said cell when said cell is not infected with said pathogen.

3. The composition of claim 1 or 2 when said stress protein is a member of the stress protein families selected from the group consisting of Hsp60, Hsp70, and Hsp90.

4. The composition of claim 1 or 2 when said stress protein is gp96.

5. The composition of claim 4, wherein said stress protein is a human stress protein.

6. The composition of claim 1 or 2 further comprising a cytokine.

7. The composition of claim 6 wherein said cytokine is selected from the group consisting of IL-1α, IL-1β, IL-2, IL-3, IL-4, IL-5, IL-6, IL-7, IL-8, IL-9, IL-10, IL-11, IL-12, IFNα, IFNβ, IFNγ, TNF , TNFβ, G-CSF, GM-CSF, GM-CSF and TGF-β.

8. The composition of claim 1 or 2, wherein said eukaryotic cell is an immortalized eukaryotic cell.

9. The composition of claim 1 or 2 wherein said stress protein is a human stress protein.

10. The composition of claim 1 or 2 wherein said pathogen is a bacteria.

11. The composition of claim 10 wherein said bacteria is selected from the group consisting of mycobacteria, rickettsia, mycoplasma, neisseria and legionella.

12. The composition of claim 1 or 2 wherein said pathogen is a protozoan.

13. The composition of claim 12 wherein said protozoan is selected from the group consisting of leishmania, trypanosoma and kokzidioa.

14. The composition of claim 1 or 2 wherein said pathogen is an intracellular parasite.

15. The composition of claim 14 wherein said parasite is selected from the group consisting of chlamydia and rickettsia.

16. A method of eliciting in a mammal an immune response against an intracellular pathogen selected from the group consisting of a bacterium, protozoan, fungus and parasite, that causes disease in said mammal, the method comprising:
  administering to said mammal a composition comprising:
    (a) an amount of a purified population of immunogenic mammalian stress protein-peptide complexes sufficient to elicit in said mammal an immune response against said pathogen, and said population comprising a complex of
      a mammalian stress protein noncovalently associated with a peptide that is present in a eukaryotic cell infected with said pathogen but not present in said cell when said cell is not infected with said pathogen; and
    (b) a pharmaceutically acceptable carrier.

17. A method of eliciting in a mammal an immune response against an intracellular pathogen selected from the group consisting of a bacterium, protozoan, fungus and parasite, that causes disease in said mammal, the method comprising:
  administering to said mammal a composition comprising:
    (a) an amount of a purified population of immunogenic mammalian stress protein-peptide complexes sufficient to elicit in said mammal an immune response against said pathogen, said population comprising a complex of
      a mammalian stress protein noncovalently associated with a peptide, said population of complexes having been isolated from a eukaryotic cell infected with said pathogen; and
    (b) a pharmaceutically acceptable carrier.

18. The method of claim 16 or 17, wherein said immune response is a cytotoxic T cell response mediated by the class I major histocompatibility complex.

19. The method of claim 16 or 17, wherein said stress protein is a member of a stress protein family selected from the group consisting of Hsp60, Hsp70, and Hsp90.

20. The method of claim 16 or 17, wherein said stress protein is gp96.

21. The method of claim 16 of 17, wherein said composition further comprises a cytokine.

22. The method of claim 21, wherein said cytokine is selected from the group consisting of IL-1α, IL-1β, IL-2, IL-3, IL-4, IL-5, IL-6, IL-7, IL-8, IL-9, IL-10, IL-11, IL-12, IFNα, IFNβ, IFNγ, TNF , TNFβ, G-CSF, GM-CSF, GM-CSF and TGF-β.

23. The method of claim 16 or 17, wherein said eukaryotic cell is an immortalized eukaryotic cell.

24. The method of claim 16 or 17, wherein said mammal is a human.

25. The method of claim 16 or 17, wherein said composition is administered prophylactically to said mammal for stimulating in said mammal a cytotoxic T cell response for preventing subsequent infection of said mammal by said pathogen.

26. The method of claim 16 or 17, wherein said composition is administered therapeutically to said mammal for stimulating in said mammal a cytotoxic T cell response against said pathogen presently infecting said mammal.

27. The method of claim 16 or 17, wherein said composition is administered to said mammal in an amount in the range of about 1 to about 1000 micrograms of complex/kg body weight of mammal/immunization.

28. The method of claim 27, wherein said amount is in range of about 100 to about 250 micrograms of complex/kg body weight of mammal/immunization.

29. The method of claim 16 or 17 wherein said mammal is a human and said stress protein is a human stress protein.

30. The method of claim 16 or 17 wherein said pathogen is a bacterium.

31. The method of claim 30 wherein said mammal is a human and said stress protein is a human stress protein.

32. The method of claim 16 or 17 wherein said same fungus.

33. The method of claim 32 wherein said mammal is a human and said stress protein is a human stress protein.

34. The method of claim 16 or 17 wherein said same protozoan.

35. The method of claim 34 wherein said mammal is a human and said stress protein is a human stress potein.

36. The method of claim 16 or 17 wherein said pathogen is a parasite.

37. The method of claim 36 wherein said mammal is a human and said stress protein is a human stress protein.

38. A composition comprising:
  (a) an amount of a purified population of immunogenic mammalian stress protein-peptide complexes sufficient to elicit in said mammal an immune response against an intracellular pathogen selected from the group consisting of a bacterium, protozoan, fungus and parasite, said population comprising a complex of
    a mammalian stress protein noncovalently associated with a peptide that is present in an eukaryotic cell transfected with a gene encoding an antigenic determinant of said pathogen but not present in said cell when said cell is not transfected with said gene; and
  (b) a pharmaceutically acceptable carrier.

39. The composition of claim 38, wherein said stress protein is a member of a stress protein family selected from the group consisting of Hsp60, Hsp70 and Hsp90.

40. The composition of claim 39, wherein said stress protein is a human stress protein.

41. The composition of claim 38, wherein said stress protein is gp96.

42. The composition of claim 38, wherein said immune response is a cytotoxic T cell response mediated by the class I major histocompatibility complex.

43. A method of eliciting in a mammal an immune response against an intracellular pathogen selected from the group consisting of a bacterium, protozoan, fungus and parasite, that causes disease in said mammal, the method comprising:
administering to said mammal a composition comprising
(a) an amount of a purified population of immunogenic mammalian stress protein-peptide complexes sufficient to elicit in said mammal an immune response against said pathogen, and said population comprising a complex of a mammalian stress protein noncovalently associated with a peptide that is present in a eukaryotic cell transfected with a gene encoding an antigenic determinant of said pathogen but not present in said cell when said cell is not transfected with said gene; and
(b) a pharmaceutically acceptable carrier.

44. A method of eliciting in a mammal an immune response against an intracellular pathogen selected from the group consisting of a bacterium, protozoan, fungus and parasite, that causes disease in said mammal, the method comprising:
administering to said mammal a composition comprising,
(a) an amount of a purified population of immunogenic mammalian stress protein-peptide complexes sufficient to elicit in said mammal an immune response against said pathogen, said population comprising a complex of a mammalian stress protein noncovalently associated with a peptide, said population of complexes having been isolated from a eukaryotic cell transfected with a gene encoding an antigenic determinant of said pathogen; and
(b) a pharmaceutically acceptable carrier.

45. The method of claim 43 or 44, wherein said immune response is a cytotoxic T cell response mediated by the class I major histocompatibility complex.

46. The method of claim 43 or 44, wherein said stress protein is a member of a stress protein family selected from the group consisting of Hsp60, Hsp70, and Hsp90.

47. The method of claim 43 or 44, wherein said stress protein is gp96.

48. The method of claim 43 or 44, wherein said composition further comprises a cytokine.

49. The method of claim 48, wherein said cytokine is selected from the group consisting of IL-1α, IL-1β, IL-2, IL-3, IL-4, IL-5, IL-6, IL-7, IL-8, IL-9, IL-10, IL-11, IL-12, IFNα, IFNβ, IFNγ, TNFα, TNFβ, G-CSF, GM-CSF and TGF-β.

50. The method of claim 43 or 44, wherein said euklkaryotic cell is an immortalized eukaryotic cell.

51. The method of claim 43 or 44, wherein said mammal is a human.

52. The method of claim 43 or 44, wherein said composition is administered prophylactically to said mammal for simulating in said mammal a cytotoxic T cell response for preventing subsequent infection of said mammal by said pathogen.

53. The method of claim 43 or 44, wherein said composition is administered therapeutically to said mammal for stimulating in said mammal a cytotoxic T cell response against said pathogen presently infecting said mammal.

54. The method of claim 43 or 44, wherein said composition is administered to said mammal in an amount in the range of about 1 to about 1000 micrograms of complex/kg body weight of mammal/immunization.

55. The method of claim 54, wherein said amount is in range of about 100 to about 250 micrograms of complex/kg body weight of mammal/immunization.

56. A composition comprising:
(a) an amount of a purified population of immunogenic human stress protein-peptide complexes sufficient to elicit in a human an immune response against an intracellular pathogen, said population comprising a complex of a human stress protein noncovalently associated with a peptide that is present in a eukaryotic cell infected with said intracellular pathogen but not present in said cell when said cell is not infected with said intracellular pathogen; and
(b) a pharmaceutically acceptable carrier.

57. A composition comprising:
a purified human stress protein-peptide complex, said complex comprising
a human stress protein noncovalently associated with a peptide that is present in a eukaryotic cell infected with an intracellular pathogen but not present in said cell when said cell is not infected with said intracellular pathogen.

58. A composition comprising:
(a) an amount of a purified population of immunogenic mammalian stress protein-peptide complexes sufficient to elicit in a mammal an immune response against a virus selected from the group consisting of hepatitis type A, hepatitis type B, hepatitis type C, varicella, adenovirus, herpes simplex type I (HSV-I), herpes simplex type II (HSV-II), rinderpest, rhinovirus, echovirus, rotavirus, respiratory syncytial virus, papilloma virus, papova virus, cytomegalovirus, echinovirus, arbovirus, huntavirus, coxsackie virus, mumps virus, measles virus, rubella virus, polio virus, human immunodeficiency virus type I (HIV-I), and human immunodeficiency virus type II (HIV-II), said population comprising a complex of
a mammalian stress protein noncovalently associated with a peptide that is present in a eukaryotic cell infected with said virus but not present in said cell when said cell is not infected with said virus; and
(b) a pharmaceutically acceptable carrier.

59. A composition comprising:
a purified mammalian stress protein-peptide complex, said complex comprising
a mammalian stress protein noncovalently associated with a peptide that is present in a eukaryotic cell infected with a virus selected from the group consisting of hepatitis type A, hepatitis type B, hepatitis type C, varicella, adenovirus, herpes simplex type I (HSV-I), herpes simplex type II (HSV-II), rinderpest, rhinovirus, echovirus, rotavirus, respiratory syncytial virus, papilloma virus, papova virus, cytomegalovirus, echinovirus, arbovirus, huntavirus, coxsackie virus, mumps virus, measles virus, rubella virus, polio virus, human immunodeficiency virus type I (HIV-I), and human immunodeficiency virus type II (HIV-II), but not present in said cell when said cell is not infected with said virus.

60. The composition of claim 56, 57, 58 or 59 wherein said stress protein is a member of a stress protein family selected from the group consisting of Hsp60, Hsp70, and Hsp90.

61. The composition of claim 56, 57, 58 or 59 wherein said stress protein is gp96.

62. The composition of claim 56, 57, 58 or 59 further comprising a cytokine.

63. The composition of claim 62 wherein said cytokine is selected from the group consisting of IL-1α, IL-1β, IL-2, IL-3, IL-4, IL-5, IL-6, IL-7, IL-8, IL-9, IL-10, IL-11, IL-12, IFNα, IFNβ, IFNγ, TNFα, TNFβ, G-CSF, GM-CSF, G-CSF and TGF-β.

64. The composition of claim 56, 57, 58 or 59, wherein said eukaryotic cell is an immortalized eukaryotic cell.

65. The composition of claim 58 or 59 wherein said mammal is a human.

66. The composition of claim 56 or 57 wherein said intracellular pathogen is a virus.

67. A method of eliciting in a human an immune response against a virus that causes disease in said human, the method comprising:
administering to said human a composition comprising:
(a) an amount of a purified population of immunogenic human stress protein-peptide complexes sufficient to elicit in said human an immune response against said virus, said population comprising a complex of
a human stress protein noncovalently associated with a peptide that is present in a eukaryotic cell infected with said virus but not present in said cell when said cell is not infected with said virus; and
(b) a pharmaceutically acceptable carrier.

68. A method of eliciting in a human an immune response against a virus that causes disease in said human, the method comprising:
administering to said human a composition comprising:
(a) an amount of a purified population of immunogenic human stress protein-peptide complexes sufficient to elicit in said human an immune response against said virus, said population comprising a complex of
a human stress protein noncovalently associated with a peptide, said population of complexes having been isolated from a eukaryotic cell infected with said virus; and
(b) a pharmaceutically acceptable carrier.

69. A method of eliciting in a mammal an immune response against a virus that causes disease in said mammal, said virus selected from the group consisting of hepatitis type A, hepatitis type B, hepatitis type C, varicella, adenovirus, herpes simplex type I (HSV-I), herpes simplex type II (HSV-II), rinderpest, rhinovirus, echovirus, rotavirus, respiratory syncytial virus, papilloma virus, papova virus, cytomegalovirus, echinovirus, arbovirus, huntavirus, coxsackie virus, mumps virus, measles virus, rubella virus, polio virus, human immunodeficiency virus type I (HIV-I), and human immunodeficiency virus type II (HIV-II), the method comprising:
administering to said mammal a composition comprising:
(a) an amount of a purified population of immunogenic mammalian stress protein-peptide complexes sufficient to elicit in said mammal an immune response against said virus, said population comprising a complex of
a mammalian stress protein noncovalently associated with a peptide that is present in a eukaryotic cell infected with said virus but not present in said cell when said cell is not infected with said virus; and
(b) a pharmaceutically acceptable carrier.

70. A method of eliciting in a mammal an immune response against a virus that causes disease in said mammal, said virus selected from the group consisting of hepatitis type A, hepatitis type B, hepatitis type C, varicella, adenovirus, herpes simplex type I (HSV-I), herpes simplex type II (HSV-II), rinderpest, rhinovirus, echovirus, rotavirus, respiratory syncytial virus, papilloma virus, papova virus, cytomegalovirus, echinovirus, arbovirus, huntavirus, coxsackie virus, mumps virus, measles virus, rubella virus, polio virus, human immunodeficiency virus type I (HIV-I), and human immunodeficiency virus type II (HIV-II), the method comprising:
administering to said mammal a composition comprising:
(a) an amount of a purified population of immunogenic mammalian stress protein-peptide complexes sufficient to elicit in said mammal an immune response against said virus, said population comprising a mammalian stress protein noncovalently associated with a peptide, said population of complexes having been isolated from a eukaryotic cell infected with said virus; and
(b) a pharmaceutically acceptable carrier.

71. The method of claim 67, 68, 69 or 70 wherein said immune response is a cytotoxic T cell response mediated by the class I major histocompatibility complex.

72. The method of claim 67, 68, 69 or 70, wherein said stress protein is a member of a stress protein family selected from the group consisting of Hsp60, Hsp70, and Hsp90.

73. The method of claim 67, 68, 69 or 70, wherein said stress protein is gp96.

74. The method of claim 67, 68, 69 or 70, wherein said composition further comprises a cytokine.

75. The method of claim 74, wherein said cytokine is selected from the group consisting of IL-1α, IL-1β, IL-2, IL-3, IL-4, IL-5, IL-6, IL-7, IL-8, IL-9, IL-10, IL-11, IL-12, IFNα, IFNβ, IFNγ, TNFα, TNFβ, G-CSF, GM-CSF, and TGF-β.

76. The method of claim 67, 68, 69 or 70, wherein said eukaryotic cell is an immortalized eukaryotic cell.

77. The method of claim 69 or 70, wherein said mammal is a human.

78. The method of claim 69 or 70, wherein said composition is administered prophylactically to said mammal for stimulating in said mammal a cytotoxic T cell response for preventing subsequent infection of said mammal by said virus.

79. The method of claim 69 or 70, wherein said composition is administered prophylactically to said human for stimulating in said human a cytotoxic T cell response for preventing subsequent infection of said human by said virus.

80. The method of claim 69 or 70 wherein said composition is administered therapeutically to said mammal for stimulating in said mammal a cytotoxic T cell response against said virus presently infecting said mammal.

81. The method of claim 67 or 68 said composition is administered therapeutically to said human for stimulating in said human a cytotoxic T cell response against said virus presently infecting said human.

82. The method of claim 69 or 70, wherein said composition is administered to said mammal in an amount in the range of about 1 to about 1000 micrograms of complex/kg body weight of mammal/immunization.

83. The method of claim 82, wherein said amount is in range of about 100 to about 250 micrograms of complex/kg body weight of mammal/immunization.

84. The method of claim 67 or 68, wherein said composition is administered to said human in an amount in the range of about 1 to about 1000 micrograms of complex/kg body weight of human/immunization.

85. The method of claim 84, wherein said amount is in range of about 100 to about 250 micrograms of complex/kg body weight of human/immunization.

86. A composition comprising:
(a) an amount of a purified population of immunogenic human stress protein-peptide complexes sufficient to elicit in a human an immune response against a virus, said population comprising a complex of a human stress protein noncovalently associated with a peptide that is present in an eukaryotic cell transfected with a gene encoding an antigenic determinant of said virus but not present in said cell when said cell is not transfected with said gene; and (b) a pharmaceutically acceptable carrier.

87. A composition comprising:

(a) an amount of a purified population of immunogenic mammalian stress protein-peptide complexes sufficient to elicit in a mammal an immune response against a virus selected from the group consisting of hepatitis type A, hepatitis type B, hepatitis type C, varicella, adenovirus, herpes simplex type I (HSV-I), herpes simplex type II (HSV-II), rinderpest, rhinovirus, echovirus, rotavirus, respiratory syncytial virus, papilloma virus, papova virus, cytomegalovirus, echinovirus, arbovirus, huntavirus, coxsackie virus, mumps virus, measles virus, rubella virus, polio virus, human immunodeficiency virus type I (HIV-I), and human immunodeficiency virus type II (HIV-II), said population comprising a complex of a mammalian stress protein noncovalently associated with a peptide that is present in an eukaryotic cell transfected with a gene encoding an antigenic determinant of said virus but not present in said cell when said cell is not transfected with said gene; and (b) a pharmaceutically acceptable carrier.

88. The composition of claim 86 or 87 wherein said stress protein is a member of the stress protein families selected from the group consisting of Hsp60, Hsp70 and Hsp90.

89. The composition of claim 86 or 87, wherein said stress protein is a gp96.

90. The composition of claim 87, wherein said stress protein is a human stress protein.

91. The composition of claim 86 or 87, wherein said immune response is a cytotoxic T cell response mediated by the class I major histocompatibility complex.

92. A method of eliciting in a human an immune response against a virus that causes disease in said human, the method comprising:

administering to said human a composition comprising,
(a) an amount of a purified population of immunogenic human stress protein-peptide complex sufficient to elicit in said mammal an immune response against said virus, said population comprising a complex of a human stress protein noncovalently associated with a peptide that is present in a eukaryotic cell transfected with a gene encoding an antigenic determinant of said virus but not present in said cell when said cell is not transfected with said gene; and
(b) a pharmaceutically acceptable carrier.

93. A method of eliciting in a human an immune response against a virus that causes disease in said human, the method comprising:

administering to said human a composition comprising
(a) an amount of a purified population of immunogenic human stress protein-peptide complex sufficient to elicit in said human an immune response against said virus, said population comprising a complex of a human stress protein noncovalently associated with a peptide, said population of complexes having been isolated from a eukaryotic cell transfected with a gene encoding an antigenic determinant of said virus; and (b) a pharmaceutically acceptable carrier.

94. A method of eliciting in a mammal an immune response against a virus that causes disease in said mammal, said virus selected from the group consisting of hepatitis type A, hepatitis type B, hepatitis type C, varicella, adenovirus, herpes simplex type I (HSV-I), herpes simplex type II (HSV-II), rinderpest, rhinovirus, echovirus, rotavirus, respiratory syncytial virus, papilloma virus, papova virus, cytomegalovirus, echinovirus, arbovirus, huntavirus, coxsackie virus, mumps virus, measles virus, rubella virus, polio virus, human immunodeficiency virus type I (HIV-I), and human immunodeficiency virus type II (HIV-II), the method comprising:

administering to said mammal a composition comprising
(a) an amount of a purified population of immunogenic mammalian stress protein-peptide complexes sufficient to elicit in said mammal an immune response against said virus, said population comprising a complex of a mammalian stress protein noncovalently associated with a peptide that is present in a eukaryotic cell transfected with a gene encoding an antigenic determinant of said virus but not present in said cell when said cell is not transfected with said gene; and
(b) a pharmaceutically acceptable carrier.

95. A method of eliciting in a mammal an immune response against a virus that causes disease in said mammal, said virus selected from the group consisting of hepatitis type A, hepatitis type B, hepatitis type C, varicella, adenovirus, herpes simplex type I (HSV-I), herpes simplex type II (HSV-II), rinderpest, rhinovirus, echovirus, rotavirus, respiratory syncytial virus, papilloma virus, papova virus, cytomegalovirus, echinovirus, arbovirus, huntavirus, coxsackie virus, mumps virus, measles virus, rubella virus, polio virus, human immunodeficiency virus type I (HIV-I), and human immunodeficiency virus type II (HIV-II), the method comprising:

administering to said mammal a composition comprising
(a) an amount of a purified population of immunogenic mammalian stress protein-peptide complex sufficient to elicit in said mammal an immune response against said virus, said population comprising a complex of a mammalian stress protein noncovalently associated with a peptide, said population of complexes having been isolated from a eukaryotic cell transfected with a gene encoding an antigenic determinant of said virus; and
(b) a pharmaceutically acceptable carrier.

96. The method of claim 92, 93, 94 or as, wherein said immune response is a cytotoxic T cell response mediated by the class I major histocompatibility complex.

97. The method of claim 92, 93, 94 or 95, wherein said stress protein is a member of a stress protein family selected from the group consisting of Hsp60, Hsp70, and Hsp90.

98. The method of claim 92, 93, 94, or 95, wherein said stress protein is gp96.

99. The method of claim 92, 93, 94 or 95, wherein said composition further comprises a cytokine.

100. The method of claim 99, wherein said cytokine is selected from the group consisting of IL-1α, IL-1β, IL-2, IL-3, IL-4, IL-5, IL-6, IL-7, IL-8, IL-9, IL-10, IL-11, IL-12, IFNα, IFNβ, IFNγ, TNFα, TNFβ, G-CSF, GM-CSF, and TGF-β.

101. The method of claim 92, 93, 94 or 95, wherein said eukaryotic cell is an immortalized eukaryotic cell.

102. The method of claim 94 or 95, wherein said mammal is a human.

103. The method of claim 92, 93, 94 or 95, wherein said composition is administered prophylactically for stimulating in said mammal a cytotoxic T cell response for preventing subsequent infection of said mammal by said virus.

104. The method of claim 92, 93, 94 or 95, wherein said composition is administered therapeutically to said mammal for stimulating in said mammal a cytotoxic T cell response against said pathogen presently infecting said mammal.

105. The method of claim 92, 93, 95 or 95, wherein said composition is administered to said mammal in an amount in the range of about 1 to about 1000 micrograms of complex/kg body weight of mammal/immunization.

106. The method of claim 105, wherein said amount is in range of about 100 to about 250 micrograms of complex/kg body weight of mammal/immunization.

107. A composition comprising:
a complex of a mammalian stress protein noncovalently bound to an immunogenic peptide, wherein the complex is the product of a process comprising noncovalently in vitro said immunogenic peptide to said stress protein, wherein said immunogenic peptide was obtained by eluting the peptide from a MHC-peptide complex isolated from an infected or transfected cell, in which the peptide is present in said cell infected with a pathogen or transfected with a gene encoding an antigenic determinant of said pathogen, but not present in said cell when said cell is not infected with said pathogen or not transfected with said gene, respectively.

108. The composition of claim 107 wherein said stress protein is a member of a stress protein family selected from the group consisting of Hsp60, Hsp70, and Hsp90.

109. The composition of claim 108 wherein said stress protein is gp96.

110. The composition of claim 108 further comprising a cytokine.

111. The composition of claim 110 wherein said cytokine is selected from the group consisting of IL-1α, IL-1β, IL-2, IL-3, IL-4, IL-5, IL-6, IL-7, IL-8, IL-9, IL-10, IL-11, IL-12, IFNα, IFNβ, IFNγ, TNFα, TNFβ, G-CSF, GM-CSF, and TGF-β.

112. The composition of claim 107 wherein said mammal is a human.

113. A method of treating an infectious disease in a mammal caused by an intracellular pathogen selected from the group consisting of a bacterium, protozoan, fungus and parasite, the method comprising:
administering to said mammal a composition comprising:
(a) an amount of a purified population of immunogenic mammalian stress protein-peptide complexes therapeutically effective to treat an infectious disease caused by said pathogen, said population comprising a complex of
a mammalian stress protein noncovalently associated with a peptide that is present in a eukaryotic cell infected with said pathogen but not present in said cell when said cell is not infected with said pathogen; and
(b) a pharmaceutically acceptable carrier.

114. A method of treating an infectious disease in a mammal caused by an intracellular pathogen selected from the group consisting of a bacterium, protozoan, fungus and parasite, the method comprising:
administering to said mammal a composition comprising:
(a) an amount of a purified population of immunogenic mammalian stress protein-peptide complexes therapeutically effective to treat an infectious disease caused by said pathogen and comprising
a mammalian stress protein noncovalently associated with a peptide, said population of complexes having been isolated from a eukaryotic cell infected with said pathogen; and
(b) a pharmaceutically acceptable carrier.

115. A method of treating an infectious disease in a mammal caused by an intracellular pathogen selected from the group consisting of a bacterium, protozoan, fungus and parasite, the method comprising:
administering to said mammal a composition comprising
(a) an amount of a purified population of immunogenic mammalian stress protein-peptide complexes therapeutically effective to treat an infectious disease caused by said pathogen, and said population comprising a complex of a mammalian stress protein noncovalently associated with a peptide that is present in a eukaryotic cell transfected with a gene encoding an antigenic determinant of said pathogen but not present in said cell when said cell is not transfected with said gene; and
(b) a pharmaceutically acceptable carrier.

116. A method of treating an infectious disease in a mammal caused by an intracellular pathogen selected from the group consisting of a bacterium, protozoan, fungus and parasite, the method comprising:
administering to said mammal a composition comprising
(a) an amount of a purified population of immunogenic mammalian stress protein-peptide complexes therapeutically effective to treat an infectious disease caused by said pathogen, said population comprising a complex of
a mammalian stress protein noncovalently associated with a peptide, said population of complexes having been isolated from a eukaryotic cell transfected with a gene encoding an antigenic determinant of said pathogen; and
(b) a pharmaceutically acceptable carrier.

117. A method of treating an infectious disease in a mammal caused by a virus, the method comprising:
administering to said mammal a composition comprising
(a) an amount of a purified population of immunogenic mammalian stress protein-peptide complexes therapeutically effective to treat an infectious disease caused by said virus, said population comprising a complex of
a mammalian stress protein noncovalently associated with a peptide that is present in a eukaryotic cell infected with said virus but not present in said cell when said cell is not infected with said virus; and
(b) a pharmaceutically acceptable carrier.

118. A method of treating an infectious disease in a mammal caused by a virus, the method comprising:
administering to said mammal a composition comprising
(a) an amount of a purified population of immunogenic mammalian stress protein-peptide complexes therapeutically effective to treat an infectious disease caused by said virus, said population comprising a complex of
a mammalian stress protein noncovalently associated with a peptide, said population of complexes having been isolated from a eukaryotic cell infected with said virus; and
(b) a pharmaceutically acceptable carrier.

119. A method of treating an infectious disease in a mammal caused by a virus, the method comprising:

administering to said mammal a composition comprising
(a) an amount of a purified population of immunogenic mammalian stress protein-peptide complexes therapeutically effective to treat an infectious disease caused by said virus, said population comprising a complex of a mammalian stress protein noncovalently associated with a peptide that is present in a eukaryotic cell transfected with a gene encoding an antigenic determinant of said virus but not present in said cell when said cell is not transfected with said gene; and
(b) a pharmaceutically acceptable carrier.

120. A method of treating an infectious disease in a mammal caused by a virus, the method comprising:
administering to said mammal a composition comprising
(a) an amount of a purified population of immunogenic mammalian stress protein-peptide complexes therapeutically effective to treat an infectious disease caused by said virus, and comprising
a mammalian stress protein noncovalently associated with a peptide, said population of complexes having been isolated from a eukaryotic cell transfected with a gene encoding an antigenic determinant of said virus; and
(b) a pharmaceutically acceptable carrier.

121. The method of claim 113, 114, 115, 116, 117, 118, 119, or 120, wherein said stress protein is a member of a stress protein family selected from the group consisting of Hsp70, and Hsp90.

122. The method of claim 113, 114, 115, 116, 117, 118, 119, or 120, wherein said stress protein is a gp96.

123. The method of claim 113, 114, 115, 116, 117, 118, 119, or 120, wherein said composition further comprises a cytokine.

124. The method of claim 123, wherein said cytokine is selected from the group consisting of IL-1α, IL-1β, IL-2, IL-3, IL-4, IL-5, IL-6, IL-7, IL-8, IL-9, IL-10, IL-11, IL-12, IFNα, IFNβ, IFNγ, TNFα, TNFβ, G-CSF, GM-CSF, and TGF-β.

125. The method of claim 113, 114, 115, 116, 117, 118, 119, or 120, wherein said eukaryotic cell is an immortalized eukaryotic cell.

126. The method of claim 113, 114, 115, 116, 117, 118, or 119, wherein said mammal is a human.

127. The method of claim 117, 118, 119, or 120, wherein said virus is selected from the group consisting of hepatitis type A, hepatitis type B, hepatitis type C, varicella, adenovirus, herpes simplex type I (HSV-I), herpes simplex type II (HSV-II), rinderpest, rhinovirus, echovirus, rotavirus, respiratory syncytial virus, papilloma virus, papova virus, cytomegalovirus, echinovirus, arbovirus, huntavirus, coxsackie virus, mumps virus, measles virus, rubella virus, polio virus, human immunodeficiency virus type I (HIV-I), and human immunodeficiency virus type II (HIV-II).

128. A method of eliciting in a mammal an immune response against an intracellular pathogen that causes disease in said mammal, the method comprising:
administering to said mammal a composition comprising
(a) an amount of a purified population of immunogenic mammalian stress protein-peptide complexes sufficient to elicit in said mammal an immune response against said pathogen, wherein the population of complexes is the product of a process comprising noncovalently complexing in vitro a population of immunogenic peptides to a stress protein, wherein said population of immunogenic peptides comprises immunogenic peptides which were obtained by eluting the peptides from MHC-peptide complexes isolated from a cell infected by said pathogen or transfected with a gene encoding an antigenic determinant of said pathogen, in which the population of immunogenic peptides comprises a peptide that is present in said cell infected with said pathogen or transfected with a gene encoding an antigenic determinant of said pathogen, but not present in said cell when said cell is not infected with said pathogen or not transfected with said gene, respectively; and
(b) a pharmaceutically acceptable carrier.

129. A method of treating an infectious disease in a mammal caused by an intracellular pathogen, the method comprising:
administering to said mammal a composition comprising:
(a) an amount of a purified population of immunogenic mammalian stress protein-peptide complexes therapeutically effective to treat an infectious disease caused by said pathogen, wherein the population of complexes is the product of a process comprising noncovalently complexing in vitro a population of immunogenic peptides to a stress protein, wherein said population of immunogenic peptide comprises immunogenic peptides which were obtained by eluting the peptides from MHC-peptide complexes isolated from a cell infected by said pathogen or transfected with a gene encoding an antigenic determinant of said pathogen, in which the population of immunogenic peptides comprises a peptide that is present in said cell infected with said pathogen or transfected with a gene encoding an antigenic determinant of said pathogen, but not present in said cell when said cell is not infected with said pathogen or not transfected with said gene, respectively; and
(b) a pharmaceutically acceptable carrier.

130. The method of claim 128, wherein said immune response is a cytotoxic T cell response is mediated by the class I major histocompatibility complex.

131. The method of claim 128 or 129, wherein said stress protein is a member of a stress protein family selected from the group consisting of Hsp60, Hsp70, and Hsp90.

132. The method of claim 128 or 129, wherein said stress protein is gp96.

133. The method of claim 128 or 129, wherein said composition further comprises a cytokine.

134. The method of claim 133, wherein said cytokine is selected from the group consisting of IL-1α, IL-1β, IL-2, IL-3, IL-4, IL-5, IL-6, IL-7, IL-8, IL-9, IL-10, IL-11, IL-12, IFNα, IFNβ, IFNγ, TNFα, TNFβ, G-CSF, GM-CSF, and TGF-β.

135. The method of claim 128 or 129, wherein said cell is an immortalized cell.

136. The method of claim 128 or 129, wherein said mammal is a human.

137. A purified, immunogenic, noncovalent complex of a mammalian stress protein and an antigenic peptide, which complex is the product of complexing said mammalian stress protein and said antigenic peptide in vitro.

138. The composition of claim 137 wherein said stress protein is a member of the stress protein families selected from the group consisting of Hsp60, Hsp70, and Hsp90.

139. The composition of claim 137 wherein said stress protein is gp96.

140. The composition of claim 137 wherein said stress protein is a human stress protein.

141. A method for eliciting in a mammal an immune response against an antigenic peptide, said method comprising administering to said mammal a composition comprising (a) an amount of a noncovalent complex of a mammalian stress protein and an antigenic peptide sufficient to elicit in said mammal an immune response against said antigenic peptide, which complex is the product of complexing said mammalian stress protein and said antigenic peptide in vitro; and (b) a pharmaceutically acceptable carrier.

142. The method of claim 141 wherein said immune response is a cytotoxic T cell response mediated by the class I major histocompatibility complex.

143. The method of claim 141 wherein said stress protein is a member of a stress protein family selected from the group consisting of Hsp60, Hsp70, and Hsp90.

144. The method of claim 141 wherein said stress protein is gp96.

145. The method of claim 141 wherein said mammal is a human.

146. The method of claim 141 wherein said composition is administered to said mammal in an amount in the range of about 1 to about 1000 micrograms of complex/kg body weight of mammal/immunization.

147. A composition for inducing a therapeutic immune response in a subject, comprising:
   a) a target antigen; and
   b) a heat shock protein;
      wherein the target antigen and the heat shock protein are combined in vitro under conditions wherein binding of target antigen to heat shock protein occurs to form a target antigen/heat shock protein complex; and
      wherein the administration of the target antigen/heat shock protein complex to the subject induces an immune response comprising a cytotoxic cellular component.

148. The composition of claim 147 wherein the heat shock protein is hsp70.

149. The composition of claim 147 wherein the heat shock protein is gp96.

150. The composition of claim 147 wherein the complex of target antigen and heat shock protein is purified.

151. A method of inducing a therapeutic immune response in a subject in need of such treatment, comprising administering to the subject a therapeutically effective amount of a composition comprising:
   a) a target antigen; and
   b) a heat shock protein;
      wherein the target antigen and heat shock protein are combined in vitro under conditions wherein binding of target antigen to heat shock protein occurs to form a target antigen/heat shock protein complex; and
      wherein the administration of the target antigen/heat shock protein complex to the subject induces an immune response comprising a cytotoxic cellular component.

152. The method of claim 151 wherein the heat shock protein is hsp70.

153. The method of of claim 151 wherein the heat shock protein is gp96.

* * * * *